US012721511B2

(12) United States Patent
Aluru et al.

(10) Patent No.: US 12,721,511 B2
(45) Date of Patent: Sep. 1, 2026

(54) INTRAOPERATIVE ENDOSCOPE CLEANING SYSTEM

(71) Applicant: Bayou Surgical, Inc., Houston, TX (US)

(72) Inventors: Rajitha Aluru, Houston, TX (US); William Cohn, Bellaire, TX (US); Jorge Salazar, Houston, TX (US); Scott Sloss, Houston, TX (US); Abdul Umaru, Houston, TX (US)

(73) Assignee: Bayou Surgical, Inc., Houston, TX (US)

( * ) Notice: Subject to any disclaimer, the term of this patent is extended or adjusted under 35 U.S.C. 154(b) by 0 days.

(21) Appl. No.: 18/929,301

(22) Filed: Oct. 28, 2024

(65) Prior Publication Data

US 2025/0261840 A1 Aug. 21, 2025

Related U.S. Application Data

(63) Continuation of application No. 18/171,172, filed on Feb. 17, 2023, now Pat. No. 12,150,625, which is a continuation of application No. 16/690,979, filed on Nov. 21, 2019, now Pat. No. 11,583,176.

(60) Provisional application No. 62/930,983, filed on Nov. 5, 2019.

(51) Int. Cl.

| | |
|---|---|
| ***A61L 2/16*** | (2006.01) |
| ***A61B 1/12*** | (2006.01) |
| ***A61B 17/34*** | (2006.01) |
| *A61L 103/15* | (2026.01) |

(52) U.S. Cl.

CPC .............. *A61B 1/126* (2013.01); *A61B 17/34* (2013.01); *A61B 17/3417* (2013.01); *A61L 2/16* (2013.01); *A61B 2562/0257* (2013.01); *A61L 2103/15* (2026.01)

(58) Field of Classification Search

CPC ..... A61B 1/126; A61B 17/34; A61B 17/3417; A61L 2/16

See application file for complete search history.

(56) References Cited

U.S. PATENT DOCUMENTS

| | | | |
|---|---|---|---|
| 2,264,746 | A | 12/1941 | Ellwood |
| 4,635,949 | A | 1/1987 | Lucas et al. |
| 4,800,869 | A | 1/1989 | Nakajima |

(Continued)

FOREIGN PATENT DOCUMENTS

| | | | |
|---|---|---|---|
| CA | 2842217 | A1 | 3/2008 |
| CN | 1905832 | A | 1/2007 |

(Continued)

OTHER PUBLICATIONS

Amazon.com: Morris Products 70332 Roller Ball Contacts, Open, Circuit/dp/B01CBVAYO2, http://www.amazon.com/Morris-Products-70332-Contacts-Circuit/dp/dp/B01CBVAYO2, downloaded Mar. 16, 2016, 8 pages.

(Continued)

*Primary Examiner* — Nathaniel C Chukwurah

(57) ABSTRACT

The disclosure is directed to methods and systems for cleaning scopes using a camera port (e.g. trocar) which has been modified to include a cleaning system. A trocar is a device designed to allow surgical instruments and tools to be quickly and easily inserted into a body cavity without contacting the surrounding tissue.

20 Claims, 17 Drawing Sheets

(56) References Cited

U.S. PATENT DOCUMENTS

| | | | | |
|---|---|---|---|---|
| 4,852,551 | A | 8/1989 | Opie et al. | |
| 5,274,874 | A | 1/1994 | Cercone et al. | |
| 5,386,817 | A | 2/1995 | Jones | |
| 5,429,596 | A | 7/1995 | Arias et al. | |
| 5,476,447 | A | 12/1995 | Noda et al. | |
| 5,573,494 | A | 11/1996 | Yabe et al. | |
| 5,575,756 | A | 11/1996 | Karasawa et al. | |
| 5,697,888 | A | 12/1997 | Kobayashi et al. | |
| 6,126,592 | A * | 10/2000 | Proch | A61B 1/127 600/129 |
| 6,126,593 | A | 10/2000 | Honda et al. | |
| 7,771,384 | B2 | 8/2010 | Ravo | |
| 8,057,443 | B2 | 11/2011 | McNeil | |
| 8,672,890 | B2 | 3/2014 | Franer et al. | |
| 8,690,764 | B2 | 4/2014 | Clark et al. | |
| 8,690,831 | B2 | 4/2014 | Duke | |
| 8,915,842 | B2 | 12/2014 | Weisenburgh, II et al. | |
| 9,078,694 | B2 | 7/2015 | Hartoumbekis et al. | |
| 9,211,059 | B2 | 12/2015 | Drach et al. | |
| 10,616,491 | B2 | 4/2020 | Haggerty et al. | |
| 11,583,176 | B2 * | 2/2023 | Aluru | A61B 17/34 |
| 11,751,759 | B2 | 9/2023 | Burt et al. | |
| 11,805,968 | B2 | 11/2023 | Aluru et al. | |
| 12,150,625 | B2 * | 11/2024 | Aluru | A61B 1/126 |
| 2005/0077689 | A1 | 4/2005 | Hueil | |
| 2006/0161045 | A1 | 7/2006 | Merril et al. | |
| 2006/0293559 | A1 | 12/2006 | Grice, III et al. | |
| 2007/0282253 | A1 | 12/2007 | Sasaki | |
| 2008/0188715 | A1 | 8/2008 | Fujimoto | |
| 2008/0255424 | A1 | 10/2008 | Durgin et al. | |
| 2009/0253966 | A1 | 10/2009 | Ichimura | |
| 2009/0270818 | A1 | 10/2009 | Duke | |
| 2009/0312783 | A1 * | 12/2009 | Whayne | A61B 18/1492 606/190 |
| 2011/0152776 | A1 | 6/2011 | Hartoumbekis et al. | |
| 2011/0230716 | A1 | 9/2011 | Fujimoto | |
| 2012/0022331 | A1 | 1/2012 | Poll et al. | |
| 2013/0053643 | A1 * | 2/2013 | Yoshida | A61B 1/126 600/114 |
| 2014/0188038 | A1 | 7/2014 | Stearns et al. | |
| 2014/0275787 | A1 | 9/2014 | Miyamoto et al. | |
| 2014/0371763 | A1 | 12/2014 | Poll et al. | |
| 2015/0190041 | A1 | 7/2015 | Suehara et al. | |
| 2017/0078583 | A1 * | 3/2017 | Haggerty | H04N 23/55 |
| 2017/0182520 | A1 | 6/2017 | Yamaya | |
| 2018/0000324 | A1 | 1/2018 | Poll et al. | |
| 2018/0078120 | A1 | 3/2018 | Poll et al. | |
| 2019/0125176 | A1 * | 5/2019 | Burt | G02B 23/2476 |
| 2019/0150722 | A1 | 5/2019 | Yamaya | |
| 2020/0163541 | A1 | 5/2020 | Holsten | |
| 2020/0375444 | A1 | 12/2020 | Coffeen et al. | |
| 2021/0127963 | A1 | 5/2021 | Aluru et al. | |
| 2021/0127964 | A1 | 5/2021 | Aluru et al. | |
| 2021/0153975 | A1 | 5/2021 | Polonsky et al. | |
| 2021/0386507 | A1 | 12/2021 | Reid et al. | |
| 2022/0192480 | A1 | 6/2022 | Burt et al. | |
| 2023/0414085 | A1 | 12/2023 | Aluru et al. | |
| 2024/0172933 | A1 | 5/2024 | Burt et al. | |
| 2024/0239018 | A1 | 7/2024 | Ohara et al. | |
| 2024/0293018 | A1 | 9/2024 | Aluru et al. | |
| 2025/0000337 | A1 | 1/2025 | Gowda et al. | |
| 2025/0000610 | A1 | 1/2025 | Houssiere et al. | |
| 2025/0115604 | A1 | 4/2025 | Quattropani et al. | |

FOREIGN PATENT DOCUMENTS

| | | | |
|---|---|---|---|
| CN | 101170941 | A | 4/2008 |
| CN | 101296648 | A | 10/2008 |
| CN | 101627894 | A | 1/2010 |
| CN | 101668474 | A | 3/2010 |
| CN | 202446249 | U | 9/2012 |
| CN | 103957769 | A | 7/2014 |
| CN | 104379045 | A | 2/2015 |
| CN | 104720733 | A | 6/2015 |
| CN | 204636289 | U | 9/2015 |
| CN | 105310636 | A | 2/2016 |
| CN | 113208549 | A | 8/2021 |
| CN | 113925440 | A | 1/2022 |
| EP | 2111808 | A2 | 10/2009 |
| EP | 2886037 | A1 | 6/2015 |
| JP | H07289501 | A | 11/1995 |
| JP | 2009261948 | A | 11/2009 |
| JP | 2013048821 | A | 3/2013 |
| JP | 2016517299 | A | 6/2016 |
| WO | WO-02100455 | A2 | 12/2002 |
| WO | WO-2006039646 | A2 | 4/2006 |
| WO | WO-2010046891 | A2 | 4/2010 |
| WO | WO-2012066992 | A1 | 5/2012 |
| WO | WO-2013012790 | A2 | 1/2013 |
| WO | WO-2013183014 | A1 | 12/2013 |
| WO | WO-2014050571 | A1 | 4/2014 |
| WO | WO-2014149472 | A1 | 9/2014 |
| WO | WO-2017184415 | A1 | 10/2017 |
| WO | WO-2022235262 | A1 | 11/2022 |
| WO | WO-2023178185 | A2 | 9/2023 |
| WO | WO-2023178209 | A2 | 9/2023 |

OTHER PUBLICATIONS

Communication—Extended European Search Report, European Patent Application No. 17786362.8, Jan. 13, 2020, 6 pages.

Extended European Search Report for European Application No. EP23192572.8 dated Sep. 13, 2023, 5 pages.

Final Office Action for U.S. Appl. No. 16/094,754 dated Apr. 13, 2023, 6 pages.

Final Office Action for U.S. Appl. No. 18/366,902 mailed Mar. 27, 2025, 10 pages.

Final Office Action issued in U.S. Appl. No. 16/094,754 mailed on Aug. 30, 2022, 20 pages.

Final Office Action issued in U.S. Appl. No. 17/692,550 dated Feb. 10, 2023, 15 pages.

First Office Action, China Patent Application No. 2017800379560, Dec. 1, 2020, with English translation, 8 pages.

Huang et al. "A comprehensive study of low-power operation in IEEE 802.15. 4. In Proceedings of the 10th ACM Symposium on Modeling, analysis, and simulation of wireless and mobile systems" Oct. 23, 2007, pp. 405-408.

Insinkerator, Food Waste Disposer, Sink Top Switch, downloaded Mar. 16, 2016, 2 pages.

International Preliminary Report on Patentability for International Application No. PCT/US2021/030700, mailed Oct. 24, 2023, 8 pages.

International Preliminary Report on Patentability for International Application No. PCT/US2023/064448 mailed Sep. 10, 2024, 10 pages.

International Preliminary Report on Patentability for International Application No. PCT/US2023/064479 mailed Sep. 10, 2024, 9 pages.

International Search Report and Written Opinion for International Application No. PCT/US2021/030700 dated Jan. 25, 2022, 16 pages.

International Search Report and Written Opinion for PCT Application No. PCT/US2023/064448 dated Oct. 16, 2023, 14 pages.

International Search Report and Written Opinion for PCT Application No. PCT/US2023/064479 dated Sep. 19, 2023, 16 pages.

International Search Report and Written Opinion, International Patent Application No. PCT/US2017/027320, Jul. 17, 2017, 12 pages.

Invitation to pay additional fees for International Application No. PCT/US2023/064448, dated Aug. 2, 2023, 3 pages.

McKenna et al., "A Novel Device Maintaining Clear Optics During Surgery", floshield.com/images/literature/Floshield-Lit_SAGES.pdf, downloaded May 23, 2019, 1 page.

MedGadget, ENDOPATH XCEL Trocar with OPTIVIEW Keeps The Lens Clean for Superior Visualization, http://www.medgadget.com/2010/03/endopath_xcel_trocar_with-optivie.. ., downloaded Mar. 16, 2016, 8 pages.

(56) References Cited

OTHER PUBLICATIONS

Non Final Office Action for U.S. Appl. No. 16/094,754 mailed on Dec. 22, 2022, 11 pages.
Non-Final Office Action for U.S. Appl. No. 16/690,979 mailed on Jul. 15, 2022, 20 pages.
Non-Final Office Action for U.S. Appl. No. 18/171,172 dated Dec. 27, 2023, 18 pages.
Non-Final Office Action for U.S. Appl. No. 18/366,902 mailed Sep. 9, 2024, 18 pages.
Non-Final Office Action for U.S. Appl. No. 18/479,702 mailed Sep. 24, 2024, 9 pages.
Non-Final Rejection for U.S. Appl. No. 17/692,550, mailed on Aug. 31, 2022, 21 pages.
Notice of Acceptance for Australian Patent Application No. AU2022202336 dated May 20, 2024, 3 pages.
Notice of Reasons for Rejection for Japanese Application No. 2023-568287 mailed Mar. 11, 2025, with English translation, 8 pages.
Notice of Reasons for Rejection issued Apr. 4, 2023 in Japanese Patent Application No. 2021-184037, with English Translation, 5 pages.
Notice of Reasons for Rejection, Japanese Patent Application No. 2018-555658, Jan. 20, 2021, with English translation, 8 pages.
Office Action for Australian Application No. AU2022202336A1 dated May 12, 2023, 04 pages.
Office Action for Australian Application No. 2017253708, mailed on Mar. 18, 2022, 4 pages.
Office Action for Australian Patent Application No. AU2022202336 dated May 7, 2024, 4 pages.
Office Action for Chinese Application No. 201780037956.0, dated Nov. 24, 2022,12 pages.
Office Action for Chinese Application No. 20178037956, mailed Jun. 10, 2022, 16 pages.
Office Action for Japanese Application No. JP2021184037, mailed Nov. 14, 2022, 6 pages.
Office Action issued in U.S. Appl. No. 16/094,754 dated Feb. 2, 2022, 1-20.
Office Action issued in U.S. Appl. No. 16/690,996, dated Jan. 24, 2023, 9 pages.
Wikipedia, "Trocar", https://en.wikipedia.org/wiki/Trocar , downloaded Mar. 16, 2016, 2 pages.
EP Application No. 23771637.8, Extended European Search Report mailed Jan. 27, 2026; Applicant Bayou Surgical, Inc.; 10 pages.
EP Application No. 23771654.3, Extended European Search Report mailed Feb. 2, 2026; Applicant Bayou Surgical, Inc.; 10 pages.
Final Office Action for U.S. Appl. No. 18/479,702 mailed Oct. 2, 2025, Inventor: Aluru et al., 10 pages.
U.S. Appl. No. 18/479,702, Non-Final Office Action mailed May 5, 2026; Inventor: Aluru, Rajitha et al.; 9 pages.

* cited by examiner 110
112

203
201
210
103
200
TISSUE
BODY CAVITY 210
304C
103
304B
304A
302

206
103
204
210

206
304C
103

304C
304B
206
3A
3A
3B
3B

206
ØD
$T_1$
204
$T_1$ > ØD

>90°
206
204

206
ØD
$T_2$
204
$T_2$ < ØD

<90°
206
204

204
206

200
210
302
304A
304B
304C
103
204
206

5B
300
210
204
5B

AXIAL
"PRIME" SENSOR
"WASH" SENSOR

RADIAL

OUTLINE OF SENSOR

DOME LENS
X-SECTION SHOWING A DOMED LENS TO GATHER LIGHT BOTH AXIALLY AND RADIALLY

SHAPED LENS (HALF-MOON)
X-SECTION SHOWING A SHAPED LENS TO GATHER LIGHT PREFERENTIALLY FROM THE RADIAL DIRECTION 15C
15C

* INDICATES POTENTIAL AREAS
FOR MOISTURE TO GET RETAINED
15F
15F

INTRAOPERATIVE ENDOSCOPE CLEANING SYSTEM

CROSS-REFERENCES TO OTHER RELATED PATENT APPLICATIONS

This patent application is a continuation of U.S. patent application Ser. No. 18/171,172, now U.S. Pat. No. 12,150,625, titled "INTRAOPERATIVE ENDOSCOPE CLEANING SYSTEM," filed Feb. 17, 2023, which is a continuation of U.S. patent application Ser. No. 16/690,979, now U.S. Pat. No. 11,583,176, titled "INTRAOPERATIVE ENDOSCOPE CLEANING SYSTEM," filed Nov. 21, 2019, which claims the benefit of U.S. Provisional Application No. 62/930,983, titled "INTRAOPERATIVE ENDOSCOPE CLEANING SYSTEM," filed on Nov. 5, 2019, the disclosure of each of which is hereby incorporated by reference in its entirety.

BACKGROUND

1. Field of the Invention

The present disclosure generally relates to endoscopes, and more particularly to a system and method for maintaining a clean endoscope during a procedure.

2. Discussion of the Related Art

An endoscope is a medical device utilized for medical procedures requiring the visualization of internal organs in a non-surgical manner generally referred to as a minimally invasive procedure. A physician may utilize an endoscope to make a diagnosis and/or to gain access to internal organs for treatment. The endoscope may be introduced into a patient's body via a natural orifice or through a small surgical incision.

An endoscope generally comprises three systems; namely, the endoscope system, the imaging system and the illumination system. All three systems must work together to give the physician the entire, and clear picture. More specifically, in order to achieve optimal results, the physician must be able to have a clear view from insertion of the endoscope, traveling to the organ site and during the entire procedure. In order to do this, the lens of the endoscope must be maintained free and clear of any obstructing material, including smears, residue, debris and condensation without the need to remove the device from the body. Minimally Invasive Devices, Inc. has developed the FloShield™ system that directs carbon dioxide gas to the tip of the scope to clear the lens from condensation, debris and smoke. CIPHER SURGICAL has developed the OpClear® device which utilizes a gas-powered saline delivery system to clean the scope lens during a procedure.

While the above-referenced devices do function to clean endoscopes, these devices require additional components and are fairly complex in design and use thereof. For example, these devices comprise additional sleeves which are sized for particular endoscopes. For each endoscope, there is a sleeve and if a physician changes endoscopes during a procedure, which is a common occurrence, a new sleeve must also be utilized. In addition, these devices are fully manual device/systems which required the physician to perform additional steps and thus divert his or her attention from the primary task.

Accordingly, there exists a need for a simple, efficient and easy to utilize system and method for maintaining a clean scope lens and field of view.

SUMMARY OF THE INVENTION

Intraoperative endoscope cleaning systems are disclosed herein. An example intraoperative endoscope cleaning system may comprise a control unit, a wash solution reservoir, a gas supply connected to the control unit and a camera port (e.g. a trocar). The trocar may be connected to the control unit and the wash solution reservoir and configured for facilitation of an endoscope into a body of a patient and for cleaning the endoscope during use.

The example trocar may comprise a main body, an inlet port, a fluid channel, a cleaning orifice and one or more sensors.

The main body of the trocar may comprise a head portion and an elongate hollow tube portion extending from the head portion and terminating at a distal end of the main body, wherein the tube portion defines a cavity configured to receive an endoscope.

A connector port may be disposed through the head portion of the main body and configured to receive a bulkhead connector. The distal end of the tube portion may comprise a shaped end having edges. For example, the shaped end may comprise a first edge and a second edge opposite the first edge. The first edge may extend further from the head portion than the second edge.

The inlet port may comprise a single inlet port or a plurality of inlet ports. The inlet port may be disposed through the head portion of the main body and configured to receive a wash solution, a gas or both. The wash solution may comprise a buffered solution comprising a bio-compatible surfactant. The gas may comprise carbon dioxide or other gases. The wash solution and gas may be selectively received or may be received successively. Other materials suitable for cleaning medical devices may be used.

The fluid channel may comprise a single fluid channel or a plurality of fluid channels. The fluid channel may be disposed in or adjacent the tube portion of the main body and in fluid communication with the inlet port to receive the wash solution, the gas or both from the inlet port.

The cleaning orifice may comprise a single cleaning orifice or a plurality of cleaning orifices. The cleaning orifice may be disposed adjacent the distal end of the tube portion of the main body and in fluid communication with the fluid channel to receive the wash solution, the gas, or both from the fluid channel and to allow the wash solution, the gas, or both to flow toward the cavity. The cleaning orifice may be disposed adjacent the first edge. The cleaning orifice may comprise an angled port formed through at least part of the tube portion of the main body. The cleaning orifice may be thin-walled. The cleaning orifice may comprise shaped orifice designs (e.g., circular, oval, rectangular, etc.).

One or more sensors may be disposed on or in the tube portion of the main body between the cleaning orifice and the head portion of the main body. The sensors may be disposed adjacent the fluid channel. The sensors may be configured to sense a position of the endoscope within the cavity. The sensors may comprise a flexible circuit board. The sensors may be self-calibrating. The sensors may be coupled with lenses, as shown in FIGS. 7A-7F. The sensors may be in communication with the control unit. The control unit may be configured to execute one or more cleaning processes in response to feedback received from the sensors. The execution of the one or more cleaning responses may be automatic. The control unit may be configured to provide ease of use features such as visual and audible feedback to the user to aid in positioning of the endoscope. The one or more cleaning processes may be or comprise a de-fog operation, a priming operation or a wash and dry operation.

The de-fog operation may comprise expelling a burst of gas through the cleaning orifice. The de-fog operation may be triggered as the endoscope is retracted into the tube portion and passes one or more of the sensors, for example the distal-most sensor.

The priming operation may comprise loading an amount of the wash solution into the fluid channel. The priming operation may be triggered as the endoscope is retracted into the tube portion beyond a threshold.

The wash and dry operation may comprise expelling the wash solution from the cleaning orifice. The wash and dry operation may be followed by gas for drying. The wash and dry operation may be two seconds or less.

Methods of cleaning endoscopes during procedures utilizing trocars are described herein. An example method may comprise defogging the endoscope, priming the cavity, washing the endoscope, drying the endoscope or combinations thereof. The example method, or certain portions of the example method, may be executed automatically.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION

Figure 1:
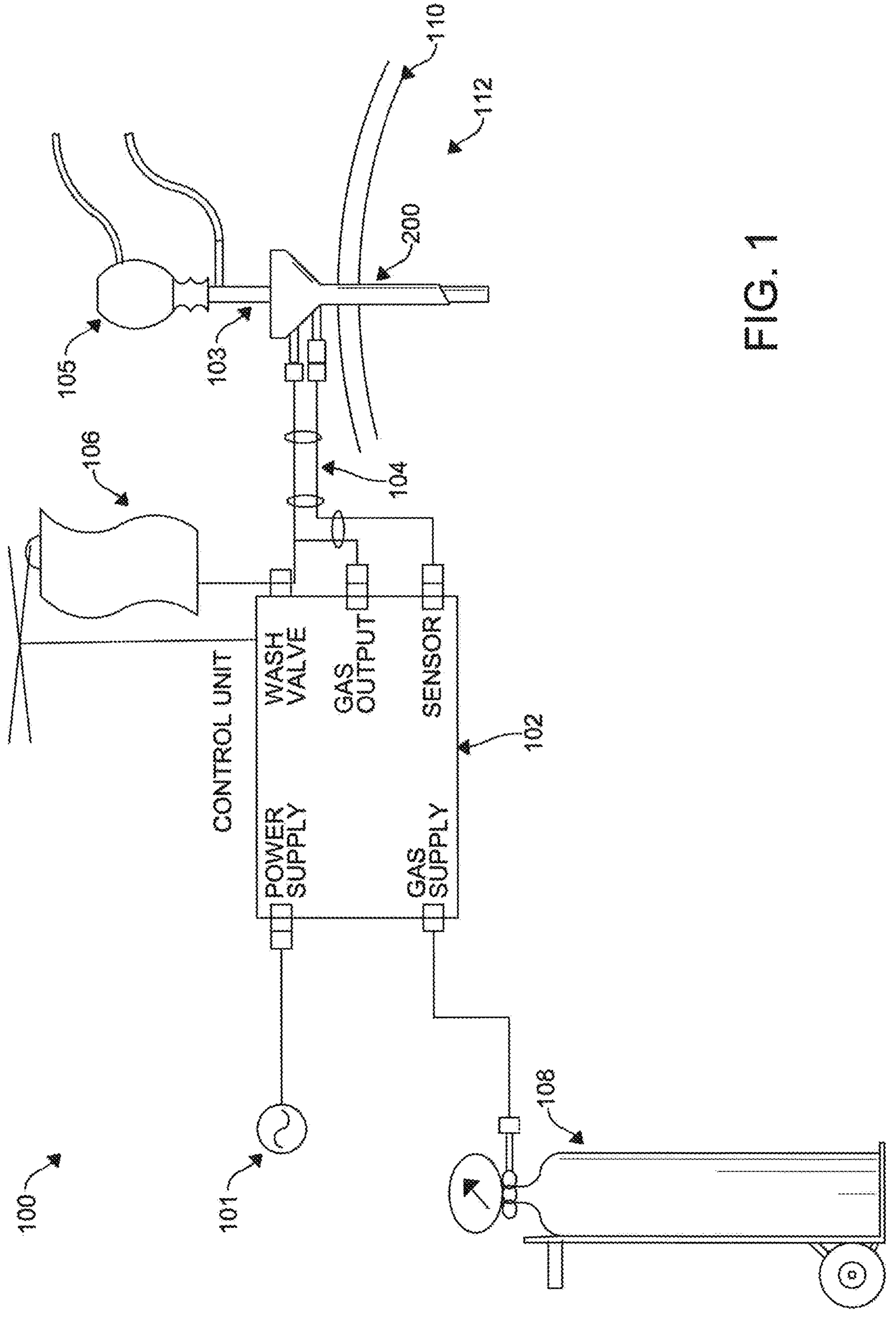
FIG. 1 is a diagrammatic representation of the endoscopic cleaning system in accordance with the present disclosure.
Figures 2A, 2B:
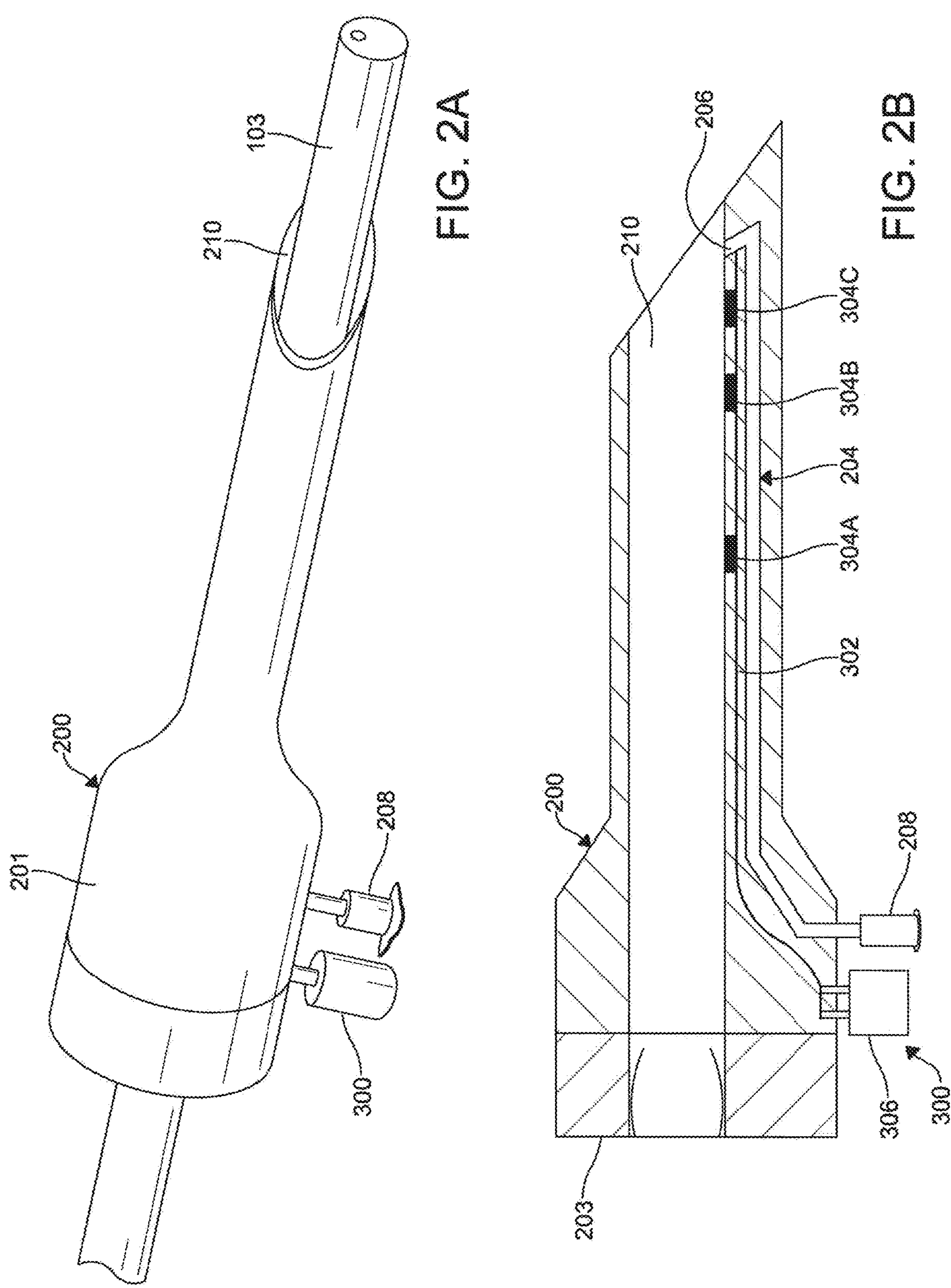
FIG. 2A is a perspective view of a trocar in accordance with the present disclosure.
FIG. 2B is a cross-sectional view of the trocar of FIG. 2A.
Figure 2C:
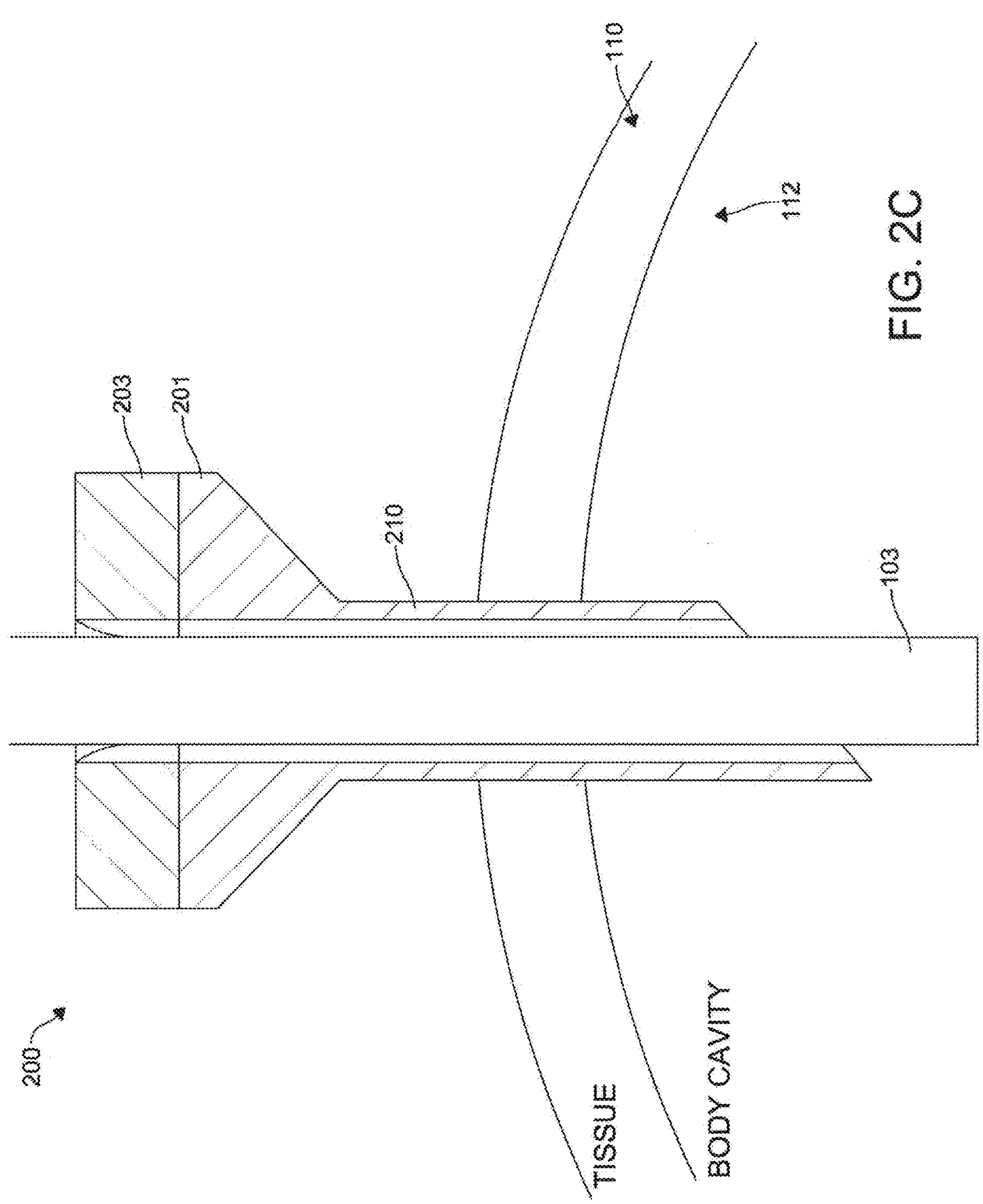
FIG. 2C is a diagrammatic representation of a trocar inserted into the body of a patient in accordance with the present disclosure.

The present disclosure provides simple and efficient methods and systems for cleaning endoscopes in-situ. An example device may be integrated into a trocar and comprise a semi-automated washing process. The systems and methods of the present disclosure are suitable for both traditional and robotic medical procedures.

The present disclosure is directed to methods and systems for cleaning scopes using a camera port (e.g. trocar) which has been modified to include a cleaning system. A trocar is a device designed to allow surgical instruments and tools to be quickly and easily inserted into a body cavity 112 without contacting the surrounding tissue 110.

Referring to FIGS. 1-5, a cleaning system 100, for example an endoscope cleaning system, of the present disclosure may comprise a trocar 200, a control unit 102, a tubing set 104, a wash solution reservoir 106 and a gas supply 108, for instance a $CO_2$ supply. The trocar 200 may comprise main body having a head portion 201 and a hollow tube portion, such as a scope lumen 210. The head portion 201 may taper to the scope lumen 210. The head portion 201 may be configured to receive a cap 203. The head portion 201 may comprise one or more ports 208, 300 to couple other devices to the trocar 200. Other configurations may be used. The scope lumen 210 may configured to receive a device such as an endoscope 103. The trocar 200 may comprise a cleaning lumen 204 (e.g., channel) that may run the length of the trocar 200 (or a portion) and exits through an orifice 206 at or adjacent the distal end thereof. The scope lumen 210 may be configured to pass through body tissue to allow a device such as the endoscope 103 to move through the trocar 200 and into a body cavity (FIG. 2C).

Figure 6:
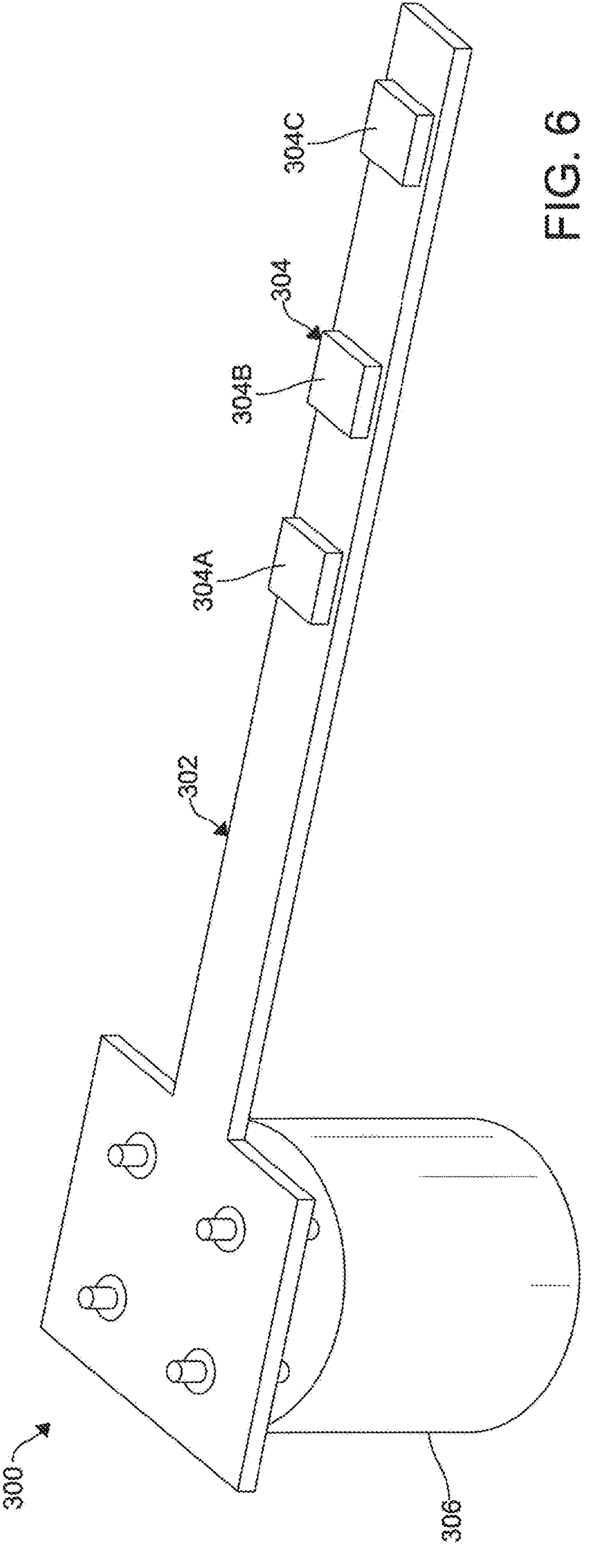
FIG. 6 is a diagrammatic representation of a sensor system.

A sensing system 300 (e.g., sensing strip FIG. 6) may be disposed in or integrated into the trocar 200 to detect the scope position and provide feedback to the control unit 102. The sensing system 300 may comprise an electrical circuit 302 and one or more sensors 304. As an illustrative example, the sensors 304 may be configured to indicate a position or function. As a further example, sensor 304A may be configured as a “scope present” sensor indicating the presence of a device in the cavity such as an endoscope. Sensor 304B may be configured as a “prime” sensor indicating a position of the scope that may trigger a priming of the wash solution channel. Sensor 304C may be configured as a “wash” sensor indicating a position of the scope that may trigger a wash process. Other positions and triggers may be used. The electrical circuit 302 may comprise a circuit board such as a flexible circuit board. Other circuits and electrical pathways may be used. The sensing system 300 may comprise a connector 306 such as a bulkhead connector. The control unit 102 may monitor one or more scope sensors 304 and upon detection of the scope 103 may activate a wash cycle, for example, comprising a wash followed by a dry. As a further example, to achieve this, the control unit 102 may prime the lumen 204 with a fixed quantity of wash solution then activate the gas dry. The gas acts as a propellant creating a very brief high energy spray (FIG. 3B) out of the orifice 206 and once the wash solution is consumed the gas acts to dry the scope 103. In this way the scope 103 is cleaned intraoperatively (without removal from the patient) and with minimal input from the operator, the operator simply requiring retraction of the scope 103 into the trocar 200.

The washing solution may comprise any suitable biocompatible material, for example, a saline solution. In preferred embodiments, the washing solution comprises a buffered solution and a surfactant. Carbon dioxide is the preferred gas to utilize for several reasons, including biocompatibility and the body's ability to absorb the carbon dioxide. The gas may be supplied from a dedicated tank or from the surgical suite supply. The gas may be supplied at a pressure in the range from about 10 to 30 psi and preferable at 30 psi.

As shown generally in FIG. 1, the control unit 102 is connected to a power supply 101 and the gas supply 108 (e.g., carbon dioxide). The control unit 102 is also connected to the trocar 200 by tubing 104 as well as the wash solution supply reservoir 106. Any number of tubes or conduits may be used to couple various elements to the trocar. The endoscope 103 with camera 105 is shown inserted into the trocar 200.

As an example, a single lumen 204 may be used to direct a wash solution 106 and pressurized gas 108 to an orifice at the distal end of the trocar. As such, the wash solution 106 and the gas 108 may be caused to flow selectively through the lumen 204, for example alternatively through the same single lumen 204 or at the same time.

The sensors 304 may be used to detect the presence of the scope which triggers an automated wash sequence. The wash sequence may comprise the priming of the system with a fixed quantity of solution (10 to 50 μl) and at the moment the sensor is triggered the pressurized gas may be activated for a fixed time period (e.g., 0.5 to 5 sec including intervening end points such as 0.5 to 1, 0.5 to 2, 0.5 to 3, 0.5 to 4, 1 to 2, or 1 to 3 secs, and the like.). The gas may serve one or more purposes, for example, as a propellant to atomize the solution into a high-energy spray (which may last e.g., 0.1 to 0.5 sec including intervening endpoints) as it exits the orifice, and/or it may act a drying system to remove excess solution from the scope (which may last e.g., 0.5 to 5 sec including intervening end points). Other sequences may be used.

Figures 3A, 3B:
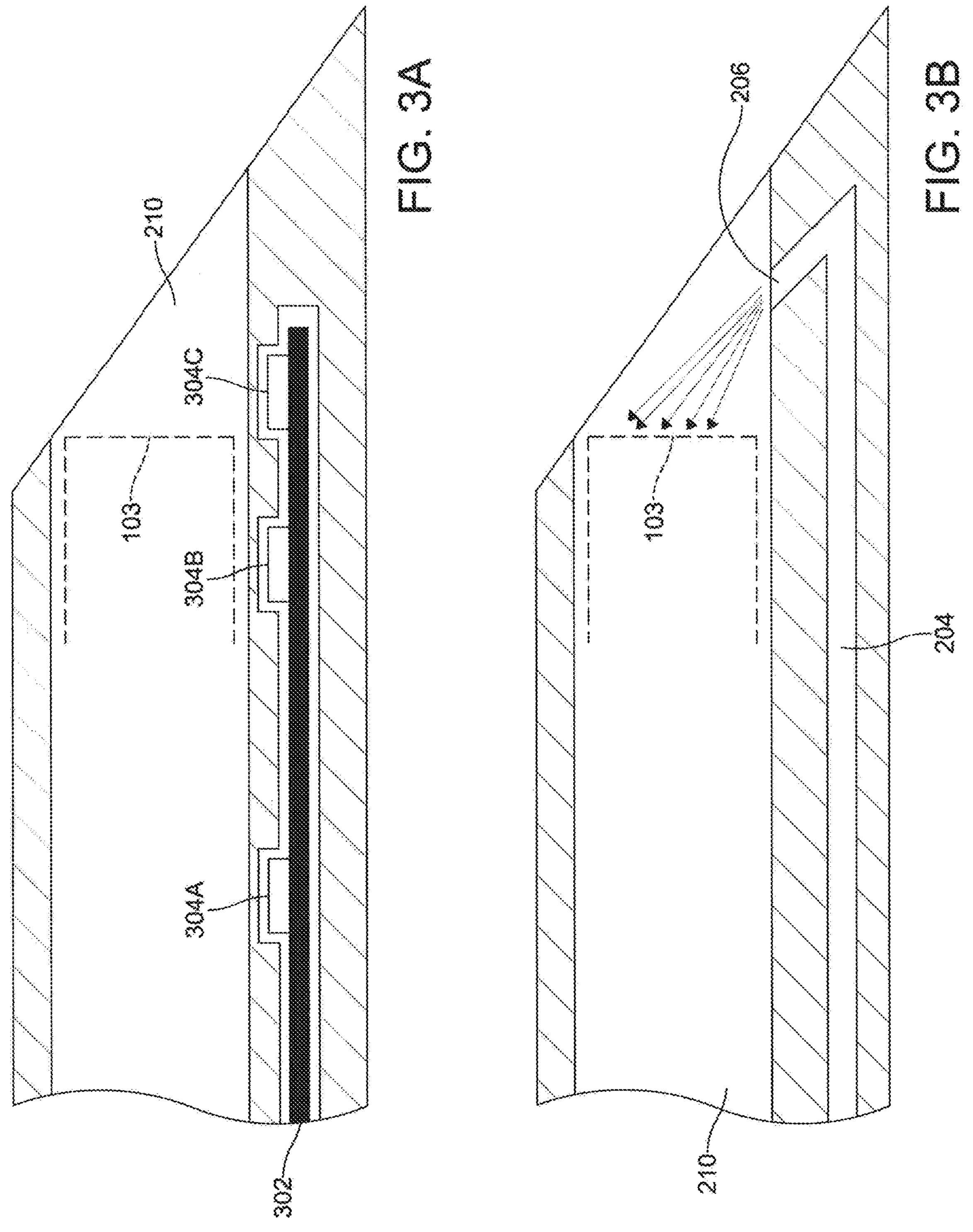
FIG. 3A is a cross-sectional view of a trocar showing a sensor configuration along line 3A-3A in FIG. 3D.
FIG. 3B is a cross-sectional view of a trocar showing a lumen configuration along line 3B-3B in FIG. 3D.
Figures 3C, 3D:
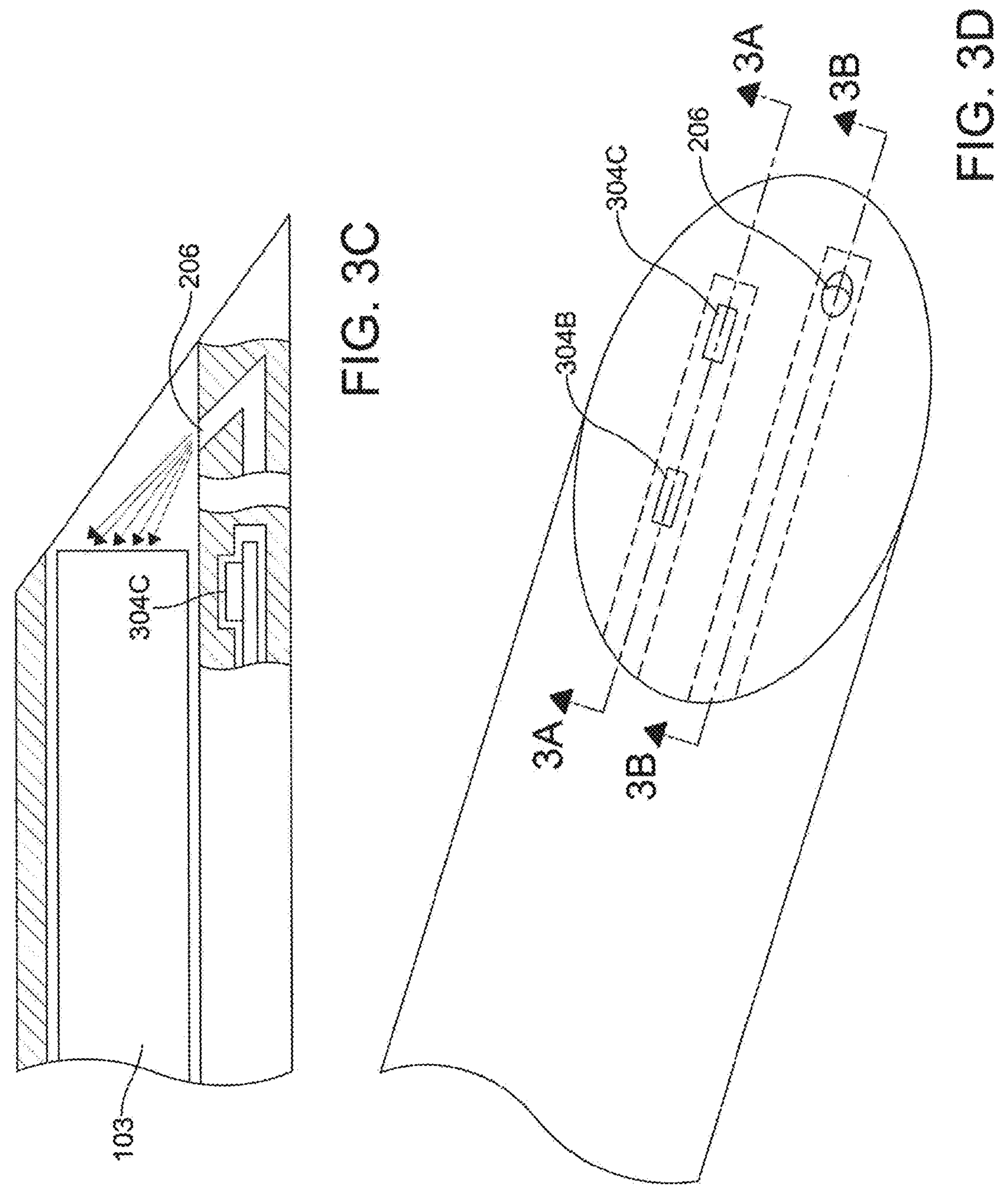
FIG. 3C is a cross-sectional view of a trocar showing a sensor and lumen configuration from FIG. 3D.
FIG. 3D is a diagrammatic representation of a trocar.
Figures 5A, 5B:
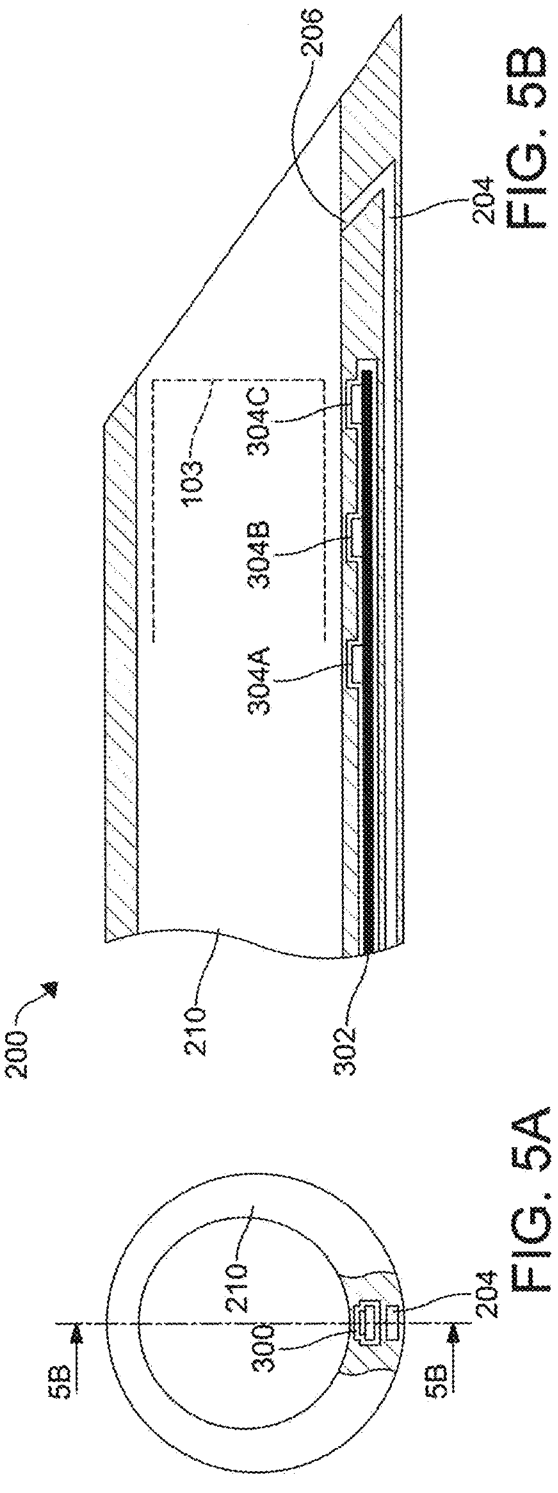
FIG. 5A is a diagrammatic representation of a trocar.
FIG. 5B is a cross-section of the trocar of FIG. 5A taken along line 5B-5B.

As an illustrative example, as shown in FIGS. 3C and 3B, a single cleaning orifice 206 may be disposed adjacent the distal end of the tube portion of the main body of a trocar and in fluid communication with the fluid channel to receive the wash solution, the gas, or both from the fluid channel and to allow the wash solution, the gas, or both to flow toward the cavity. One or more sensors 304 may be disposed on or in the tube portion of the main body between the cleaning orifice 206 and the head portion of the main body, the one or more sensors 304 configured to sense a position of the endoscope 103 within the cavity. Although various arrangements may be used, the sensors 304 may be disposed inline above or below the cleaning orifice 206 (FIGS. 5A-5B). Other arrangements include the sensors 304 being arranged along a longitudinal axis in line with the cleaning orifice 206.

The system may be used with minimal input from the operator hence the use of sensors to automatically detect the scope and activate the wash sequence. Other exemplary embodiments of this design replace the sensors with switches which the operator actuates to activate the wash. This design may be further simplified by the operator manually actuating valves to control the solution and gas supply thus removing the controller from the design. It is important to note that any combination of the above may be utilized in accordance with the present disclosure.

Figure 14:
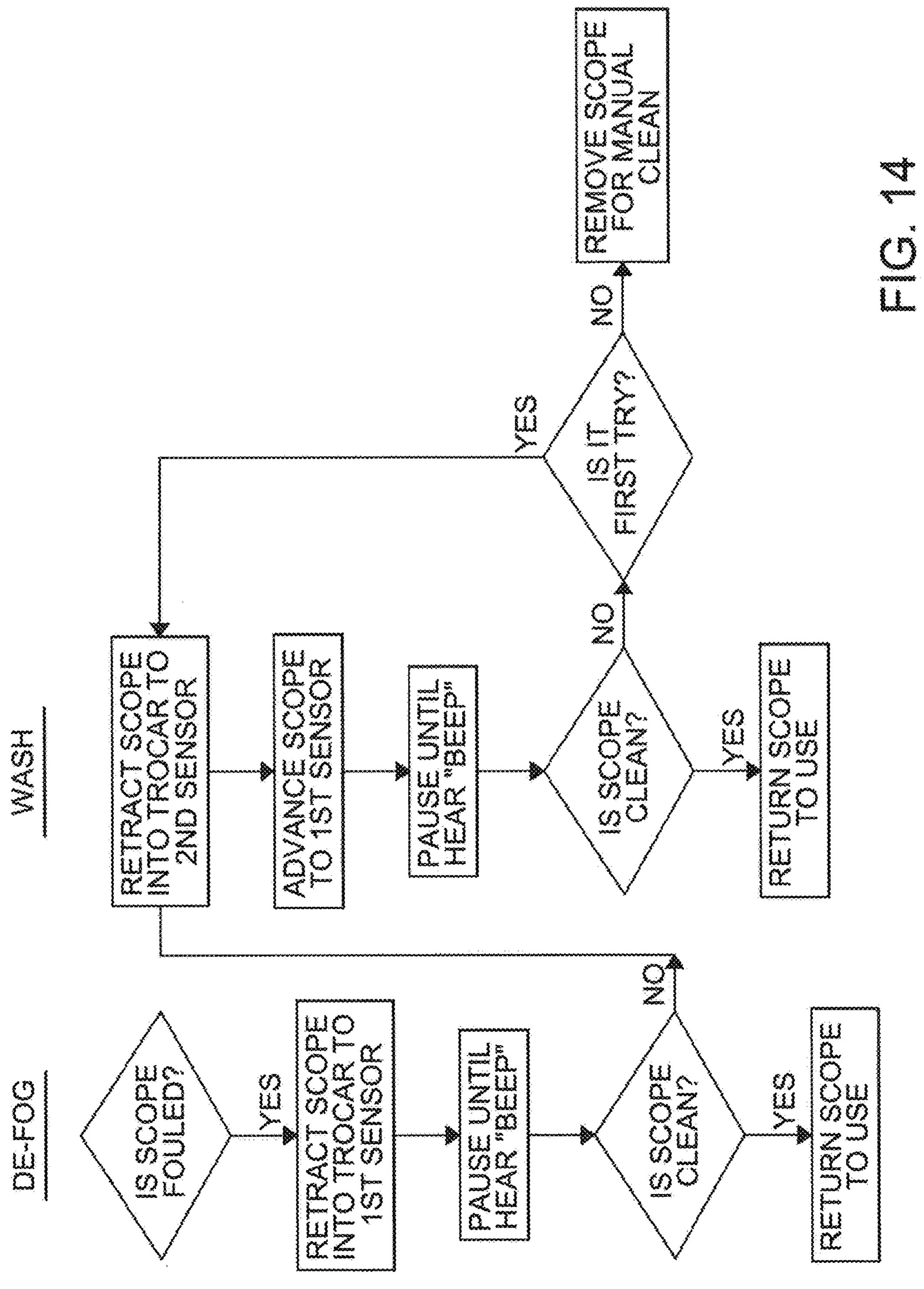
FIG. 14 is a flow chart of the process in accordance with the present disclosure.

In an aspect, the controller may enable both operation of the unit and the level of washing to be defined by the user needs. Multiple modes of operation may be pre-programmed into the controller which may then be selected by the user. For example: if the type of procedure experiences a high rate of fogging then a de-fog only mode may be selected or if there is a large build-up of debris on the scope, for example, caused by the use of energy devices then a deep-clean mode may be activated which delivers a large wash volume to the scope. FIG. 14 describes or illustrates this process in flowchart form. Various modes of operation can be envisioned to address different types of cleaning modes in addition to different ways of interacting with the system. For example: some users may find it easier to perform a wash by positioning the scope at the wash sensor and holding the scope at this position while the controller goes through its programmed sequence whereas another user may prefer to control the wash steps e.g. positioning the scope at the wash sensor triggers a dry only sequence and to trigger a full clean the user has to retract the scope further into the trocar to activate the prime sensor then extend the scope to the wash sensor to perform the full clean.

Other alternate exemplary embodiments of the trocar design are possible to improve the performance of the system. For example, multiple orifice designs to create multi-directional sprays useful for scopes with angled faces or featured faces and use of small branches from the main lumen (which have built-in restrictions to reduce the flow) to provide multiple drying ports to improve the ability of the system to dry angled of features scope faces.

A significant challenge with a cleaning system using sprays is to eliminate or minimize the amount of residual moisture that remains in the scope lumen after the spray has ended. This residual moisture has the potential to contaminate the drying sequence resulting in an incomplete dry (water droplets on the scope lens) thus compromising the cleaning.

Careful design of the lumen such as minimizing the tortuosity of the lumen path and removing the potential areas for solution to collect may reduce the potential for residual moisture however it is difficult to remove completely.

The preferred design of the trocar of the present disclosure includes a mode for the purpose of performing a dry only. In this mode when a specific sensor is triggered the system performs a gas dry only. This dry only process can be extremely quick and is effective at removing a light build-up of moisture on the scope face including drops of residual moisture, condensation or blood transfer.

Another exemplary embodiment of the trocar of the present disclosure which is designed to tackle residual moisture is the use of a secondary lumen for gas which would be used only for drying. Switching from the main lumen after washing i.e. immediately after the majority of the spray has been delivered during washing would result in a quick and effective dry with the added benefit that the gas pressure could be reduced.

There is a desire to keep the outer diameter of a trocar as small as possible to minimize the size of the incision in the patient as larger incisions are known to be associated with increased pain and a higher risk of hernia. A challenge with the trocar design of the present disclosure is how to implement the lumen and orifice with minimal impact on the outer diameter of the trocar.

Figures 4A, 4B, 4C, 4D, 4E:
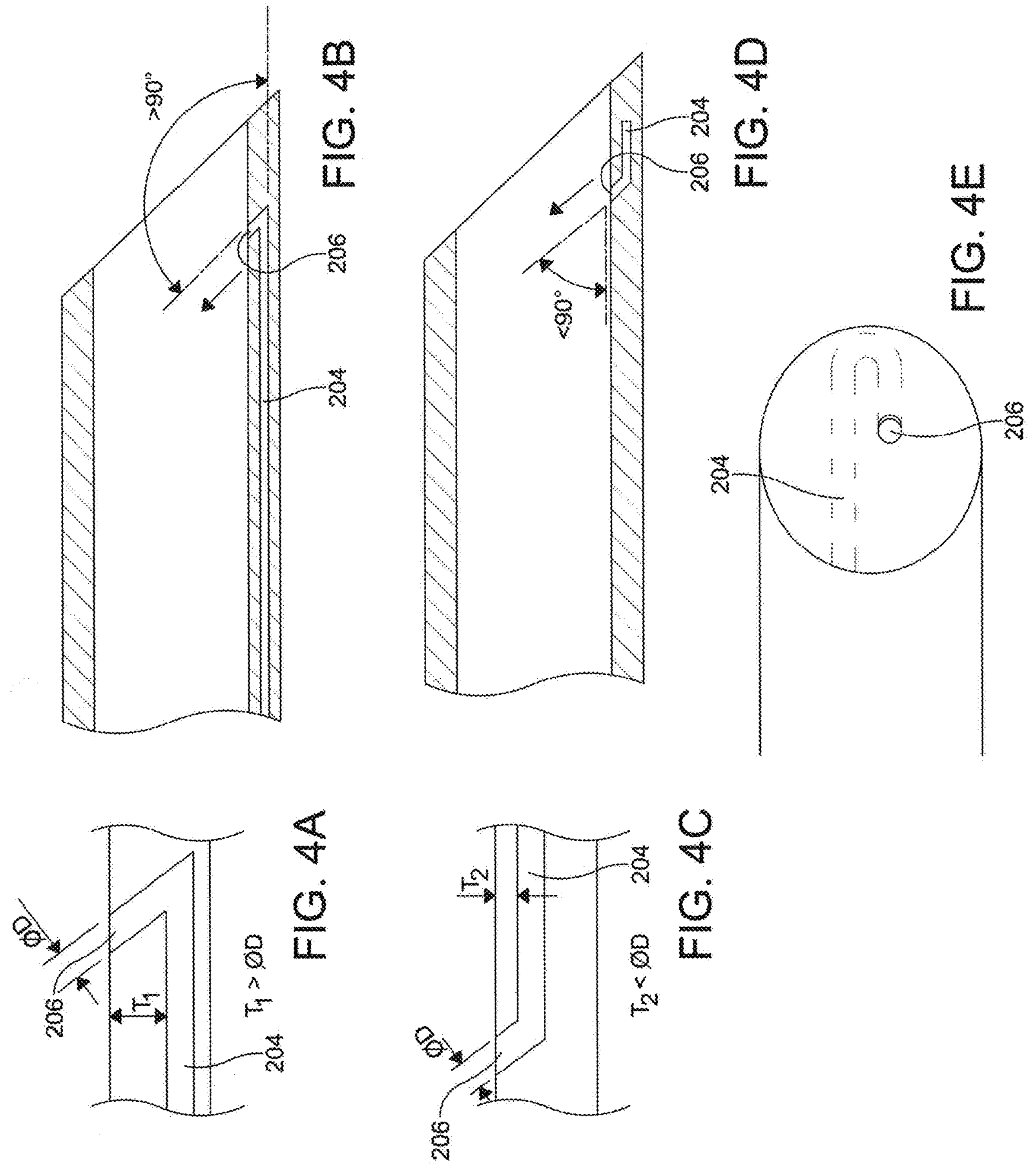
FIGS. 4A-4E are diagrammatic representations of thin walled orifice designs of a trocar in accordance with the present disclosure.

As shown in FIGS. 4A-4E, the orifice 206 may be angled to face the scope. As an example, the direction of the lumen 204 and/or 206 may be arranged such that the output angle of fluid from the orifice is greater than 90° (typically 110° to 170°) relative to the axis of the lumen 204 connecting to the orifice. Other angles and arrangements may be used, as illustrated in FIGS. 4C-4E. To create such a significant reorientation may require that the length of the orifice to be greater than or equal to the diameter of the orifice. As shown in FIG. 4A, certain arrangements may benefit from a thickness T1 that is greater than a respective outside diameter of the orifice 206. For a typical orifice diameter of 1.0 mm to 1.6 mm this adds significant thickness to the trocar. If the wall thickness is less than the length of the orifice, then the extent of reorientation is significantly reduced.

To achieve the thinnest possible trocar wall, the design of the present disclosure utilizes two different techniques. In the first technique as shown in FIGS. 4C, 4D and 4E, the circular x-section of the trocar is maintained, the scope lumen is positioned eccentric to the center of the trocar. The cleaning lumen is located within the thickest part of the trocar wall. As the lumen approaches the distal end of the trocar it is reversed in direction before existing through the orifice. Using this approach, the orifice only requires redirection of the spray to be less than 90° (typically 20° to 70°) meaning that the wall thickness may be less than the orifice diameter as shown in FIG. 4C where T2<the respective outside diameter of the orifice. In the second technique the scope lumen is kept concentric with the outer diameter and the outer diameter of the trocar is locally thickened to create a rib running the length of the trocar. The cleaning lumen and sensor strip are positioned within this rib in stacked configuration with the sensor strip positioned between the inner wall of the trocar and the cleaning lumen. This separation naturally creates the required length for the orifice to direct the spray.

One aspect of the system design is the ability to reliably detect the position of the scope within the trocar given the sources of variation in the different types of scopes commercially available e.g. scopes are available from arrange of different manufacturers, in different specifications such as viewing angle and light pattern and the use of different lighting sources such as halogen or LED.

One embodiment uses light receptive sensors to detect the emitted light from the scope which provide an analogue output in response to the level of light incident upon the sensor. Other types of sensors considered include photo-reflective, through-beam and inductive proximity. The light receptive sensors provide the best balance in terms of low package size, low cost and simplicity.

To account for the variation in sensors and the different levels of light (pattern and brightness) from different scopes it is beneficial to calibrate the system on first use. To achieve this, the control unit monitors incident light on the first scope insertion and based upon the peak level measured from the sensor one can apply a calibration factor to normalize the sensors signal or adjust the trigger threshold to set the voltage at which each sensor triggers e.g. using a pre-defined formula such as given by $$\text{Threshold}=80\%\times\text{Peak Voltage}.$$

In addition to using a dynamic threshold to account for variation one can also use the different transitions of the sensor to suit a particular purpose. For example, when one simply wants to detect the presence of a scope one can apply a low threshold to the sensor signal which provides a very sensitive signal of scope presence; however, where one wants to detect when a sensor has reached a position one can use the off transition i.e. when the scope has passed the sensor and the light is cut off.

In one embodiment the sensors are located on the dry side of the trocar (behind the inner wall of the trocar) for isolation from the fouling material and wash solution thus the trocar wall is manufactured from a transparent material such as polycarbonate or polypropylene. It is then possible to feature the wall of the trocar to create lenses to either capture additional light (radially and axially) improving the sensitivity of the sensors or to improve the positional sensitivity of the sensors by capturing light preferentially in the radial axis. Both techniques are useful in the trocar design e.g. the purpose of the 'scope present' sensor is to detect a scope so benefits from a lens to capture more light and the 'wash' sensor is to trigger a wash at a precise location so benefits from a shaped lens.

One aspect of the system design is providing feedback to the user to help them position the scope in the right position for cleaning. The sensors ensure that the wash cycle is triggered at the right time however because the scope positioning is manual there exists significant opportunity for the user to stop the scope outside of the optimal position. In this case it is possible that the wash efficacy will be compromised e.g. the scope is out of position such that it covers the wash port then no washing will occur. To aid the user target this position reliably it is beneficial to provide feedback such that the user can quickly get close to the approximate position then carefully locate the optimal position e.g. allow the user to quickly retract the scope and be alerted that they are close allowing them to slow the scope move in preparation for stopping.

One solution to this is audible feedback or visual feedback e.g. flashing lights on the control unit or a positional indicator overlaid on the scope display.

The current trocar sensors may be used to give a very coarse estimate of position e.g. warning sensor to give an alert that about to reach wash position followed by the wash position sensor altering the user to stop. Due to the analogue nature of the sensors it is possible to interpolate the actual position of the sensor which provides a finer (higher resolution) estimate of position. This information can be used to provide improved feedback to the user. For example: this positional information may be used to vary the tone of an audible signal or change the rate of beeping (like the reverse sensor in an automobile) thus providing a continuously variable feedback to the user until they reach the target position.

For an effective cleaning cycle, it has been found that the optimal position for washing and drying is at the distal end of the trocar. In this position the debris from the washing and drying process may be effectively expelled from the trocar. This prevents the build-up of debris within the trocar which can cause refouling of a clean scope and makes the scope drying process more efficient due to the minimal wash solution remaining after a wash.

One aspect of the trocar of the present disclosure uses an initial burst of gas (termed de-fog mode) to clean the scope. This burst of gas has been shown to be highly effective at cleaning scopes when the fouling material doesn't leave a film on the surface of the scope such as condensation, splashing from irrigation solution or blood. For all other types of fouling this burst of gas is highly effective at removing the bulk of the foulant from the scope which makes the subsequent wash process easier and more efficient.

Figures 7A, 7B:
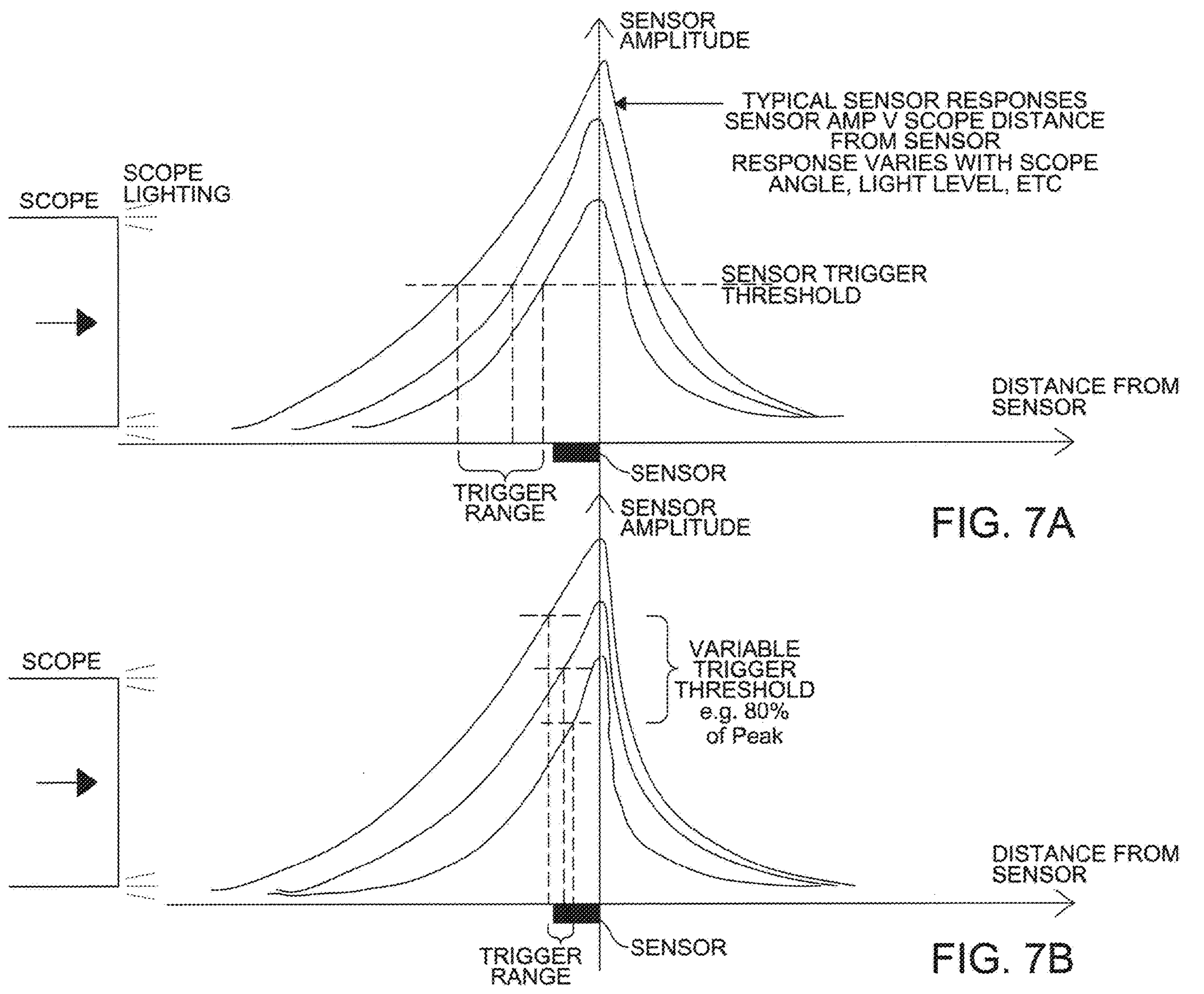
FIGS. 7A-7B are plots of example sensor settings.
Figures 8A, 8B, 8C, 8D, 8E, 8F:
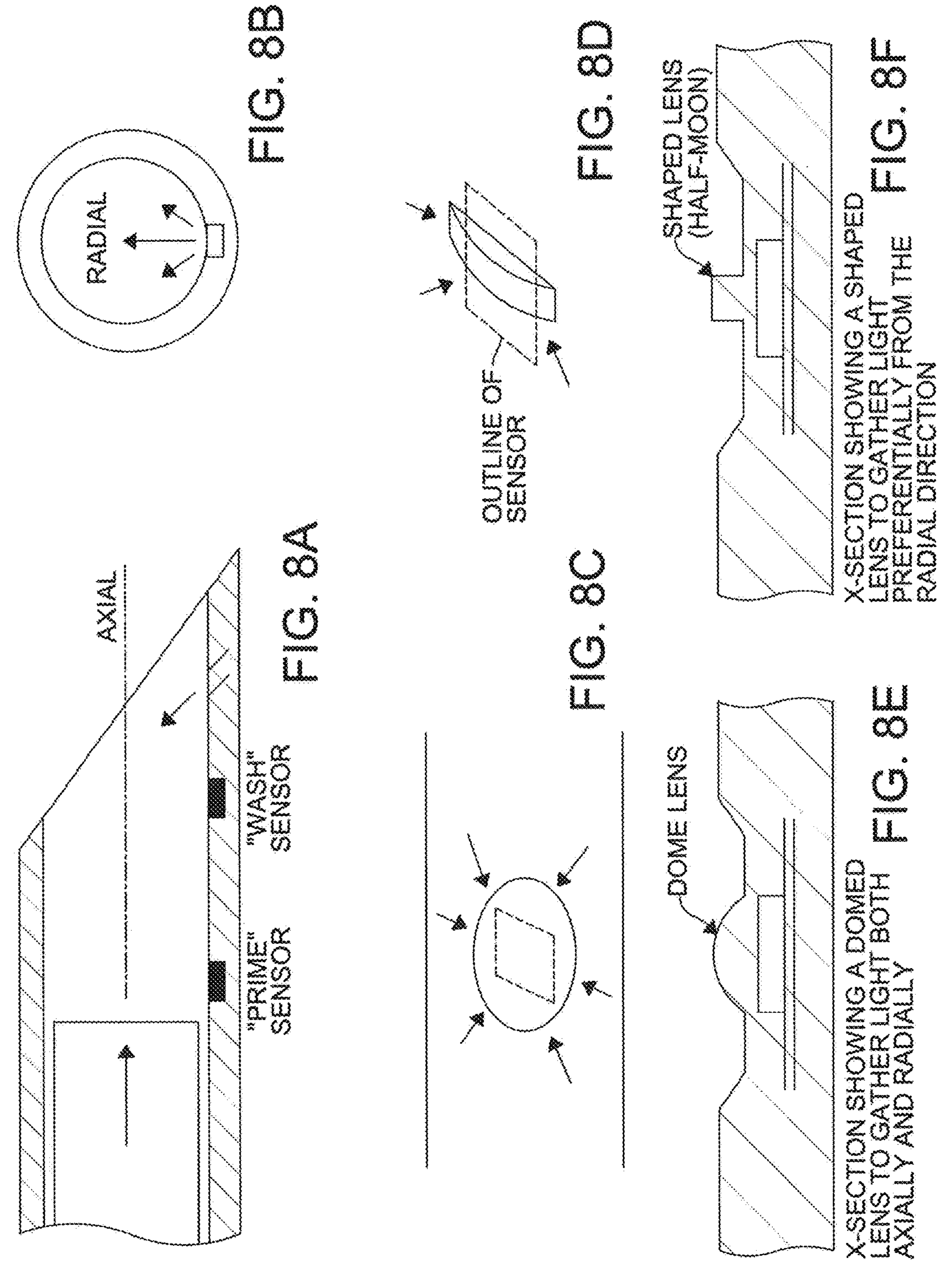
FIGS. 8A-8F are diagrammatic representations of sensor configurations with FIGS. 8E-8F including lenses.

One aspect of the system design may comprise providing an easy to use device that does not require the user to press any buttons for the process of calibration, scope insertion or cleaning cycle. In some embodiments of the present system the trocar comprises a "present" sensor (FIG. 7) for the purpose of detecting the initial insertion of the scope. Other devices and systems may be used.

By monitoring the rate of change in the sensor signal the control unit may determine if the scope is being inserted into the trocar or being removed. i.e. if the sensor signal is increasing the scope if being inserted and if the sensor signal is decreasing then the scope if being removed.

By using this sensor, the system may disable the washing cycle when the scope is first inserted into the trocar and perform a different function such as the calibration sequence detailed earlier. And conversely, the system may use this sensor input to disable the washing cycle when a scope if being removed from the trocar e.g. when the user is changing the scope type which is a common occurrence during a procedure.

As described earlier, the system may be used with scopes with different viewing angles (FIG. 9). The variation in scope angle poses a challenge for the design of the system when only using one cleaning orifice because the relationship between the cleaning orifice and the scope face to be cleaned changes significantly.

One solution to this challenge is the use of a plurality of orifices arranged circumferentially within the trocar providing effective washing irrespective of the scope rotation however this adds significantly complexity to the design of the trocar and potentially an increase in the consumption of wash solution and gas. A design that retains the simplicity of a single orifice trocar while providing an effective wash is highly preferred.

Figures 9A, 9B, 9C, 9D, 9E, 9F, 9G, 9H, 9I:
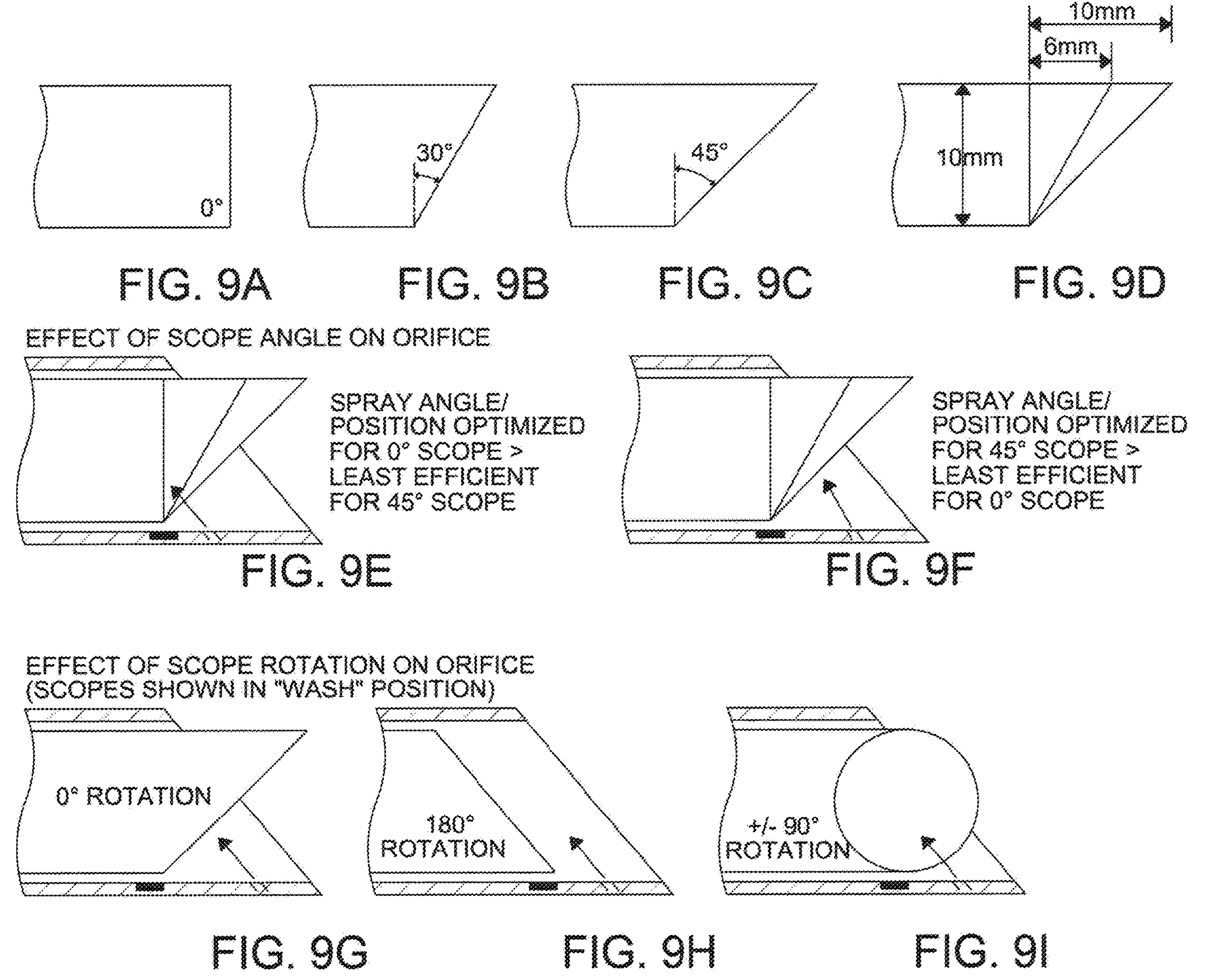
FIGS. 9A-9I are diagrammatic representations of angled endoscopes in accordance with the present disclosure.

There are at least two challenges with angled scopes: 1) the relationship between the scope face to be cleaned and the fixed orifice changes and 2) the angled scopes are asymmetric meaning that if the scopes are rotated the relationship between the scope face and the orifice changes. These challenges are described in FIG. 9. FIGS. 9A-9D show a typical range of scope angles commercially available. FIG. 9E demonstrates that when the orifice is positioned for the optimal relationship for a 0° scope then the positioning is compromised for an angled scope. FIG. 9F shows the inverse situation where the orifice is positioned to suit a 45° scope and the relationship to the 0° scope is compromised.

The angled scopes pose the additional challenge in that as they are rotated within the trocar the orientation of the scope face (to be cleaned) to the orifice changes. FIG. 9G shows the scope in the ideal relationship with the orifice directly aligned to the scope whereas FIG. 9H shows the scope in the worst orientation which, in this example, the orifice does not impinge on the scope meaning the scope clean would be ineffective. FIG. 9I shows the interim case where the scope is rotated mid-way between the optimal and worst-case orientations to help visualize the decrease in cleaning efficacy expected as the scope is rotated angle changes.

Figures 10A, 10B:
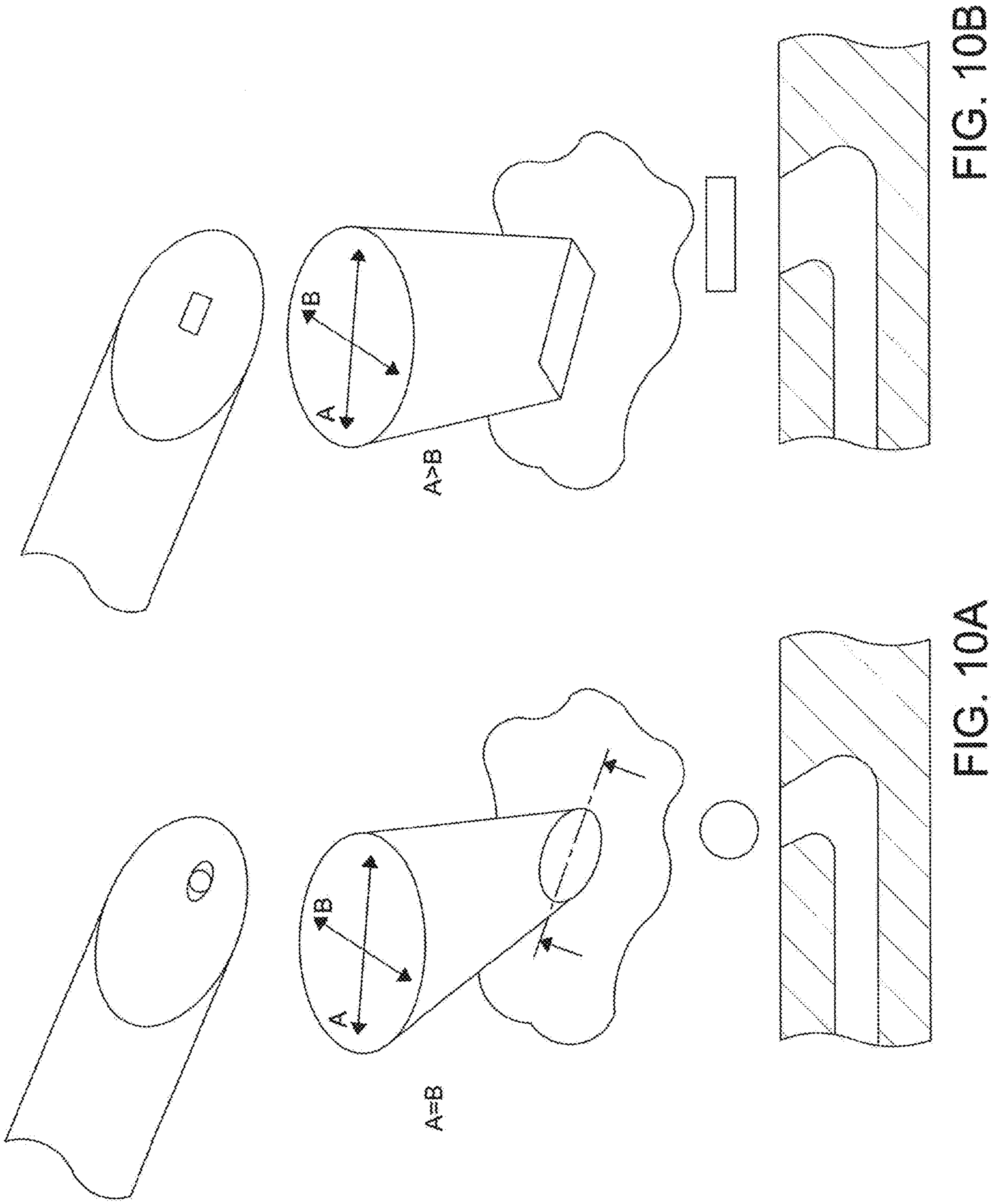
FIGS. 10A-10B are diagrammatic representations of spray orifice designs in accordance with the present disclosure.

To address these problems, the trocar may comprise the following features: The spray orifice geometry (FIG. 10A-10B) is changed to create a shaped spray which spreads the spray out over a large area to accommodate the differences between the scopes e.g. by using a rectangular or elliptical orifice the spray pattern can be flattened from a cone to a fan.

Figure 13:
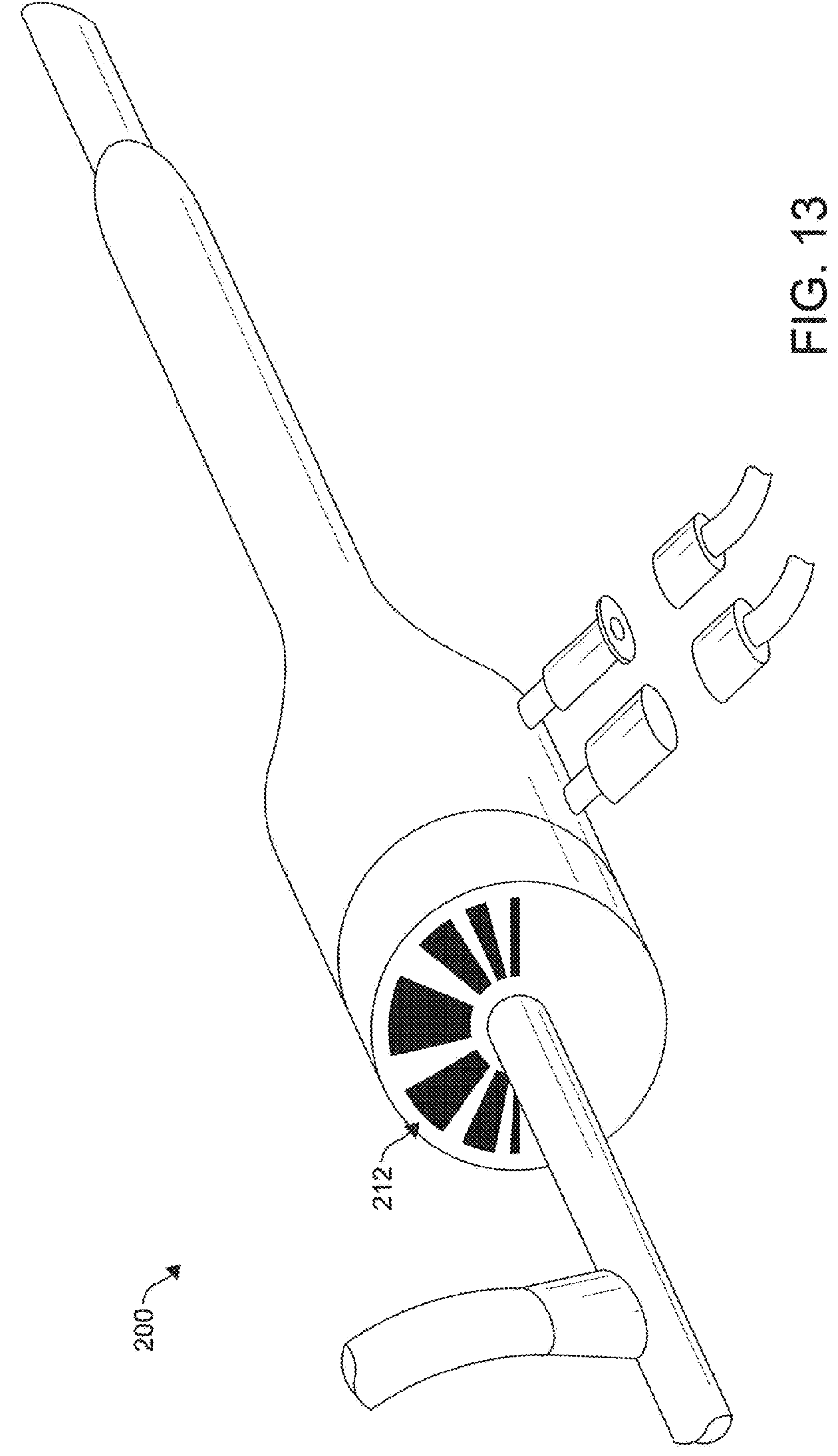
FIG. 13 is a diagrammatic representation of trocar external graphics in accordance with the present disclosure.

One solution to the rotation of the scopes is to ask the user to twist the scope to the optimal position at the same time that the scope is retracted into the trocar for washing. To aid this process graphics 212 can be printed onto the exterior of the trocar (FIG. 13) to give the user a visual cue to alignment.

Figures 11A, 11B:
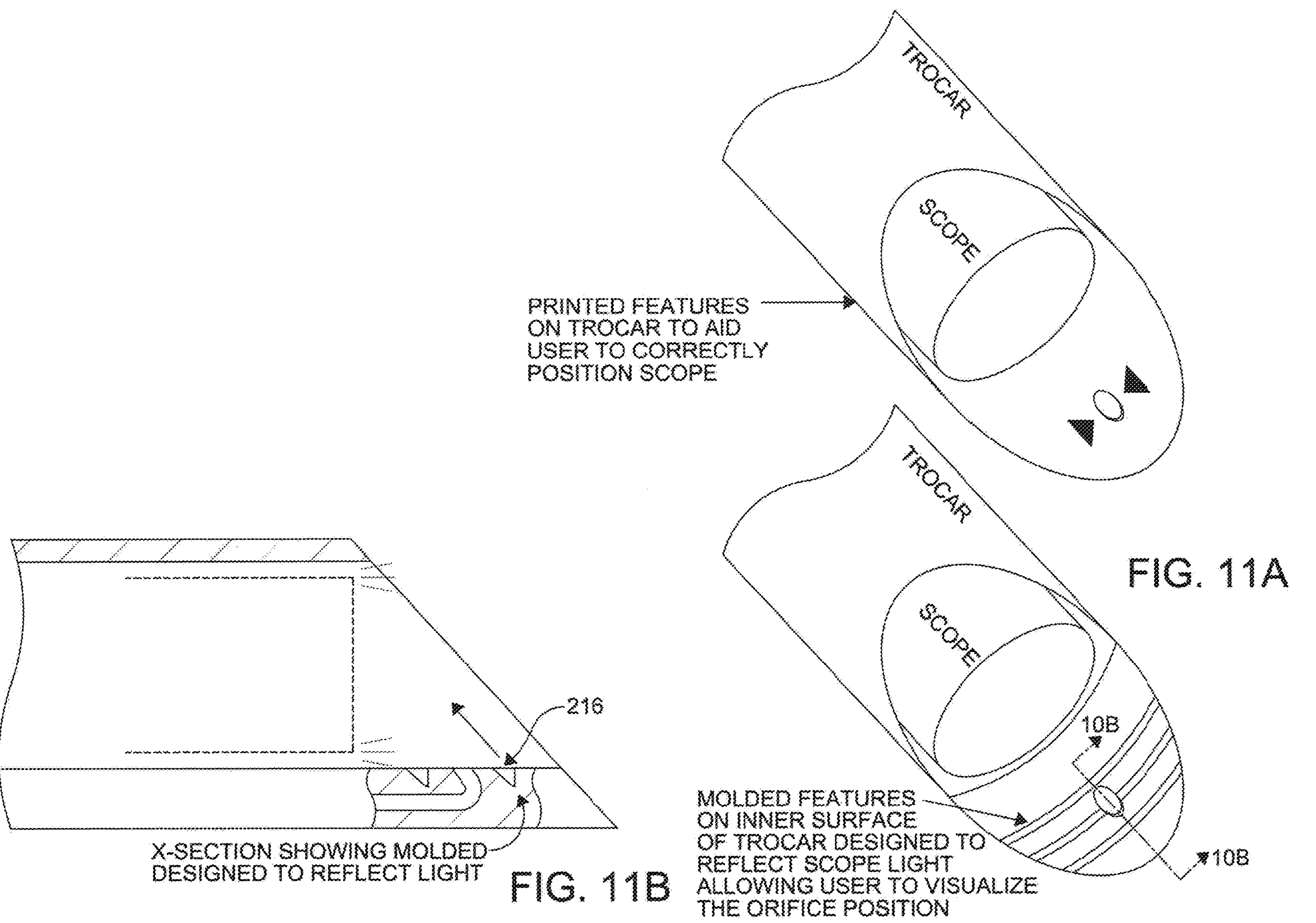
FIGS. 11A-11B are diagrammatic representations of trocar internal graphics in accordance with the present disclosure.
Figure 12:
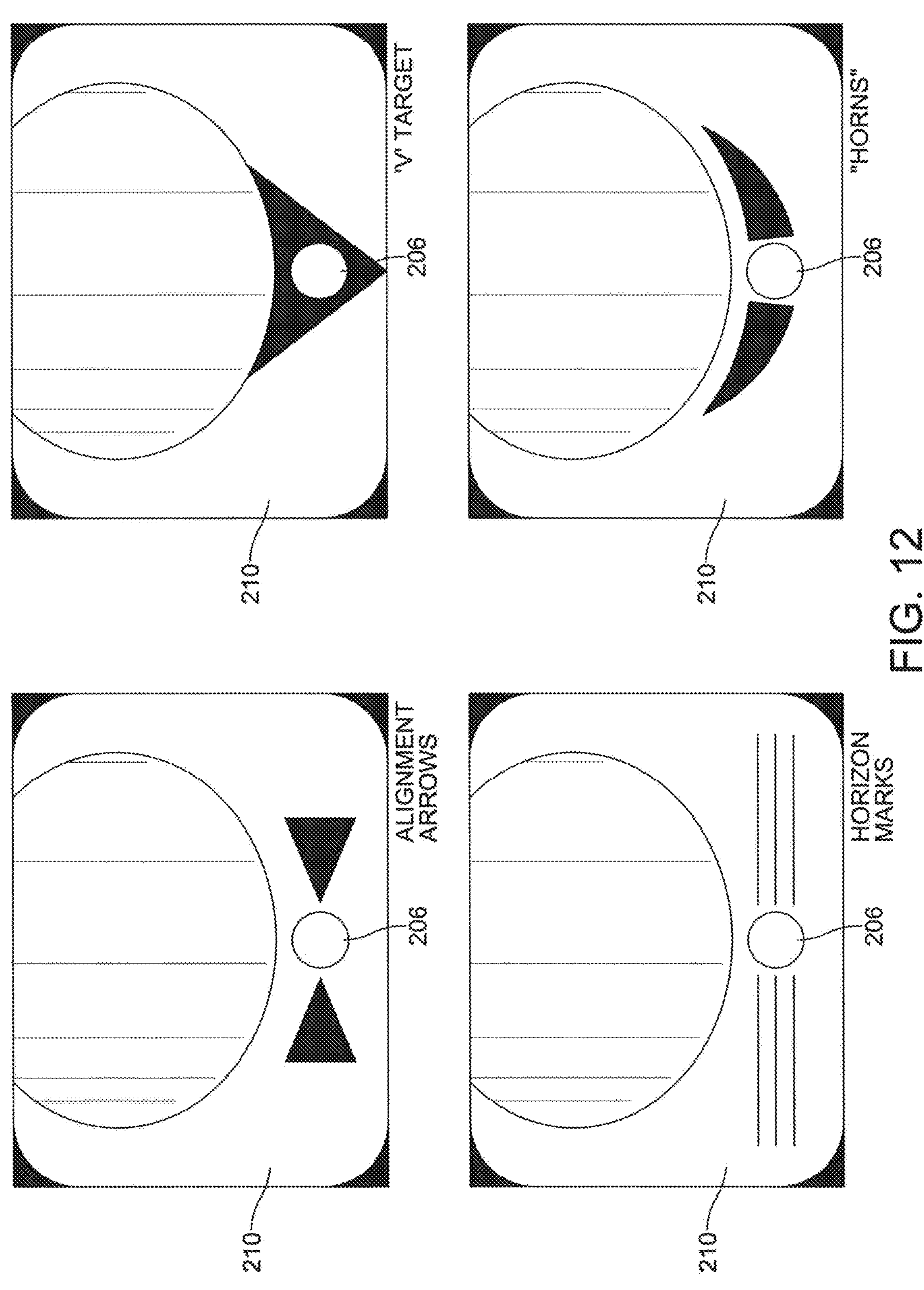
FIG. 12 shows diagrammatic representations of trocar internal graphics in accordance with the present disclosure.

The interior of the trocar (FIGS. 11-12) is featured to provide visual indication of position such that if the user has adequate visibility (or if visibility improves during the washing sequence) the user can see this target allowing the user to adjust the position of the scope for optimal cleaning. These features can be markings 214 that are embossed or printed onto the surface of the trocar or can be incorporated into the body of the trocar such a way that the features 216 reflect the light from the scope to provide a highly visible target.

The present disclosure provides functions and features that may be utilized to efficiently and effectively clean an endoscope during a procedure. The cleaning system of the present disclosure utilizes a single trocar which allows a user to clean an endoscope during a procedure with minimal requirements on the user.

The present disclosure may utilize a trocar with single lumen and orifice. The single lumen and orifice of the present disclosure provides a method of channeling a wash solution and pressurized gas from a common inlet port through a common lumen to a common spray orifice for the purpose of cleaning an endoscope.

The present disclosure may utilize an endoscope cleaning system comprising a wash solution and pressurized gas. The wash solution and pressurized gas may be utilized in a method of delivering a small volume of wash solution to a spray orifice, atomizing the solution into a transient spray followed by a continuous flow of gas for the purpose of cleaning an endoscope.

The present disclosure includes a method for minimizing and addressing residual moisture on the lens. More specifically, the present disclosure utilizes a method for minimizing residual moisture build-up in a common lumen to prevent the residual moisture compromising the drying portion of the cleaning cycle. Pressurized gas without washing solution may be utilized for drying.

Figures 15A, 15B, 15C, 15D, 15E, 15F:
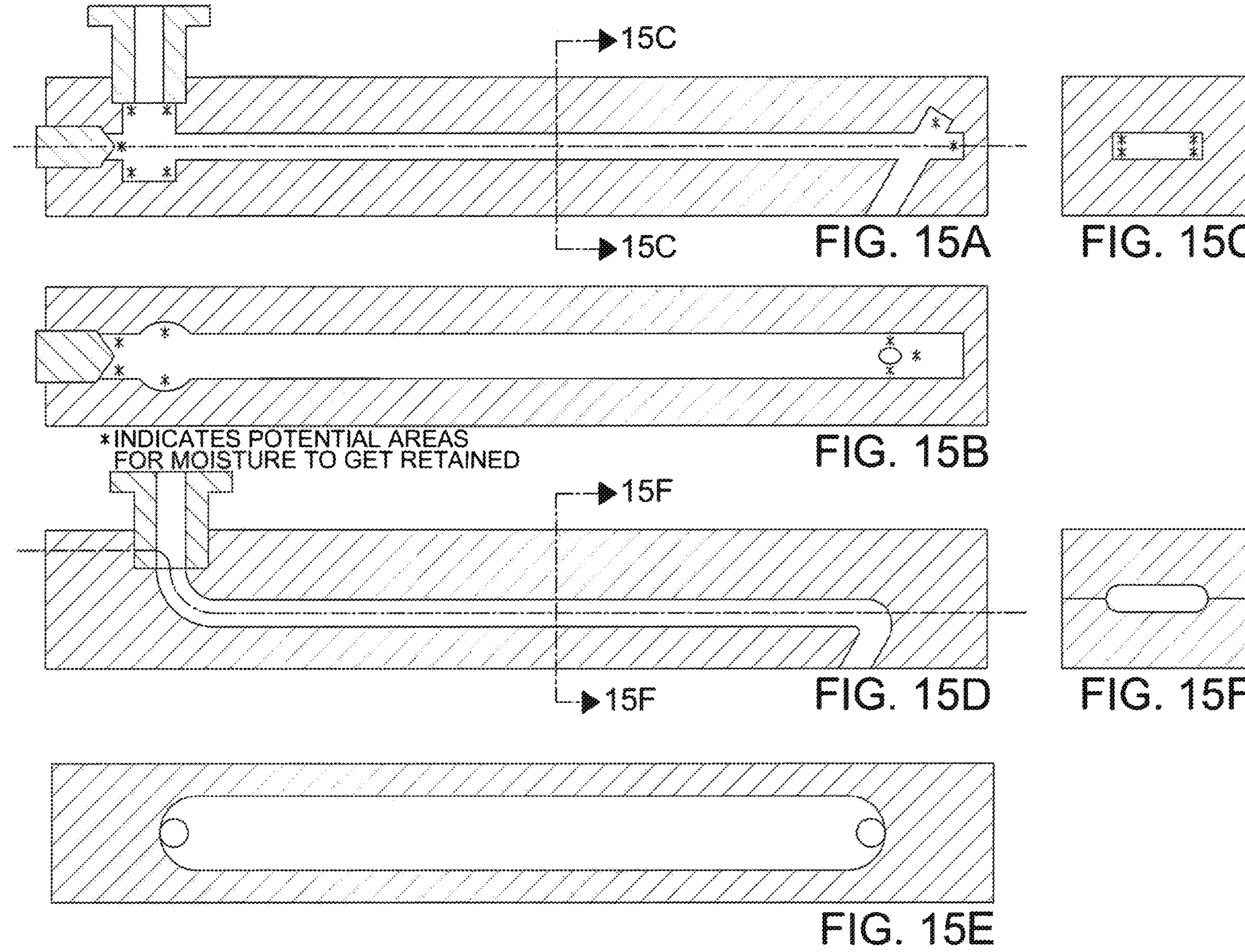
FIGS. 15A-15C illustrate an example lumen with features that cause moisture retention
FIGS. 15D-15F illustrate an example lumen with rounded edges and smooth transition between surfaces to minimize retention of moisture.

As shown in FIG. 15 the lumen is designed and manufactured in such a way to remove any edges or steps in the fluid path which can trap or retain moisture as the wash solution is propelled through the lumen. As shown in FIGS. 15A-15C, a typical lumen design may allow moisture (designated with *) to get trapped in areas on the lumen. As shown in FIGS. 15D-15F, a two-piece design may minimize retention of moisture. As an example, edges may be removed from the fluid path, which may minimize retention or buildup of moisture when compared to a stepped or hard edge design. Such lumen may be created using injection molding for example. However, other methods may be used.

The present disclosure comprises a method for creating a reverse spray angle in a thin-walled device. Methods are described for creating a spray angle that enables the spray direction to be redirected to a greater angle than if simply using the length of the orifice as the primary means of re-direction.

The present disclosure includes a method for detecting an endoscope using its emitted light. More specifically, the present disclosure utilizes a method of detecting the presence and position of an endoscope using the light emitted from the endoscope for the purpose of automatically triggering the respective step in the cleaning cycle. This eliminates the user having to initiate the process.

The present disclosure also includes a method for automatically calibrating sensors. More specifically, a method for automatically calibrating the sensors during the initial endoscope insertion into the trocar provides for accommodating the variation in endoscope lighting caused by endoscope type, endoscope angle, light source and light brightness for the purpose of achieving a reliable and repeatable cleaning system.

The present disclosure also comprises methods to aid the user in positioning the scope for cleaning. Methods are described for providing audible and visual feedback to the user for the purpose of aiding the user in positioning the endoscope in the optimal position for an effective cleaning cycle.

The present disclosure also comprises controlled spray geometry for addressing the challenges with angled endoscopes. A method and associated system is utilized to control the spray geometry from the cleaning orifice for the purpose of creating a spray pattern that is suited to different endoscope angles.

The present disclosure still further includes methods for improving the sensitivity of the endoscope's sensors to light level and position. A method utilizing different lens designs created in the wall of the trocar may improve the sensitivity at detecting the presence of an endoscope and to improve the sensitivity at the detecting the position of the endoscope.

The present disclosure still further comprises a method for interpolating the endoscope position between sensors for improved user feedback. A method using the analogue output from the endoscope sensors to estimate the scope position will result in a higher resolution than provided by the sensor signal alone for the purpose of providing improved feedback to the user on endoscope position.

Intraoperative endoscope cleaning systems are disclosed herein. An example intraoperative endoscope cleaning system may comprise a control unit, a wash solution reservoir, a gas supply connected to the control unit and a camera port (e.g. a trocar). The trocar may be connected to the control unit and the wash solution reservoir and configured for facilitation of an endoscope into a body of a patient and for cleaning the endoscope during use.

The example trocar may comprise a main body, an inlet port, a fluid channel, a cleaning orifice and one or more sensors.

The main body of the trocar may comprise a head portion and an elongate hollow tube portion extending from the head portion and terminating at a distal end of the main body, wherein the tube portion defines a cavity configured to receive an endoscope.

A connector port may be disposed through the head portion of the main body and configured to receive a bulkhead connector. The distal end of the tube portion may comprise a shaped end having edges. For example, the shaped end may comprise a first edge and a second edge opposite the first edge. The first edge may extend further from the head portion than the second edge.

The inlet port may comprise a single inlet port or a plurality of inlet ports. The inlet port may be disposed through the head portion of the main body and configured to receive a wash solution, a gas or both. The wash solution may comprise a buffered solution comprising a bio-compatible surfactant. The gas may comprise carbon dioxide or other gases. The wash solution and gas may be selectively received or may be received successively. Other materials suitable for cleaning medical devices may be used.

The fluid channel may comprise a single fluid channel or a plurality of fluid channels. The fluid channel may be disposed in or adjacent the tube portion of the main body and in fluid communication with the inlet port to receive the wash solution, the gas or both from the inlet port.

The cleaning orifice may comprise a single cleaning orifice only or a plurality of cleaning orifices. The cleaning orifice may be disposed adjacent the distal end of the tube portion of the main body and in fluid communication with the fluid channel to receive the wash solution, the gas, or both from the fluid channel and to allow the wash solution, the gas, or both to flow toward the cavity. The cleaning orifice may be disposed adjacent the first edge. The cleaning orifice may comprise an angled port formed through at least part of the tube portion of the main body. The cleaning orifice may be thin-walled. The cleaning orifice may comprise shaped orifice designs.

One or more sensors may be disposed on or in the tube portion of the main body between the cleaning orifice and the head portion of the main body. The sensors may be disposed adjacent the fluid channel. The sensors may be configured to sense a position of the endoscope within the cavity. The sensors may comprise a flexible circuit board. The sensors may be self-calibrating. The sensors may be coupled with lenses. The sensors may be in communication with the control unit. The control unit may be configured to execute one or more cleaning processes in response to feedback received from the sensors. The execution of the one or more cleaning responses may be automatic. The control unit may be configured to provide ease of use features such as visual and audible feedback to the user to aid in positioning of the endoscope. The one or more cleaning processes may be or comprise a de-fog operation, a priming operation or a wash and dry operation.

The de-fog operation may comprise expelling a burst of gas through the cleaning orifice. The de-fog operation may be triggered as the endoscope is retracted into the tube portion and passes one or more of the sensors, for example the distal-most sensor.

The priming operation may comprise loading an amount of the wash solution into the fluid channel. The priming operation may be triggered as the endoscope is retracted into the tube portion beyond a threshold.

The wash and dry operation may comprise expelling the wash solution from the cleaning orifice. The wash and dry operation may be followed by gas for drying. The wash and dry operation may be improved over conventional methods. The wash and dry operation may be five seconds or less, four seconds or less, or three seconds or less. Other times may be achieved.

Methods of cleaning endoscopes during procedures utilizing trocars are described herein. An example method may comprise defogging the endoscope, priming the cavity, washing the endoscope, drying the endoscope or combinations thereof. The example method, or certain portions of the example method, may be executed automatically. Certain procedures may be included or excluded. For example, a method may comprise defogging without priming or washing. Other procedures may be used or customized.

Although shown and described in what is believed to be the most practical and preferred embodiments, it is apparent that departures from specific designs and methods described and shown will suggest themselves to those skilled in the art and may be used without departing from the spirit and scope of the invention. The present disclosure is not restricted to the particular constructions described and illustrated but should be constructed to cohere with all modifications that may fall within the scope of the appended claims.

What is claimed is:

1. An apparatus, comprising:

a main body defining a lumen configured to receive an endoscope, the main body having a shaped end configured to be disposed in a body lumen, the shaped end including a first edge and a second edge opposite the first edge, the first edge extending further distally than the second edge, the shaped end configured to allow the endoscope to extend distal to the first and second edges and into the body lumen;

an inlet port disposed on a proximal portion of the main body and configured to receive a wash solution and a gas; and a cleaning orifice in fluid communication with the inlet port, the cleaning orifice being disposed proximal of the first edge at a position distal to the second edge, the cleaning orifice being angled relative to a longitudinal axis of the main body and being configured to deliver the wash solution and the gas into the lumen as an atomized spray to clean a distal end of the endoscope.

2. The apparatus of claim 1, wherein the cleaning orifice is angled proximally such that an output angle of the wash solution and the gas is greater than 90 degrees relative to the longitudinal axis of the main body.

3. The apparatus of claim 1, wherein the cleaning orifice is configured to deliver the wash solution and the gas in a direction towards the distal end of the endoscope.

4. The apparatus of claim 1, wherein the cleaning orifice is further configured to deliver additional gas into the lumen after delivering the wash solution to at least partially dry a surface of the endoscope.

5. The apparatus of claim 1, wherein the main body further includes a fluid channel configured to fluidically couple the inlet port to the cleaning orifice, the fluid channel extending within a wall of the main body from the proximal portion of the main body to the first edge.

6. The apparatus of claim 5, wherein the fluid channel has smooth edges without stepped or hard edges to avoid trapping or retaining moisture as the wash solution and the gas are delivered through the fluid channel.

7. The apparatus of claim 1, further comprising a control unit operatively coupled to valves that are configured to be coupled to a gas supply and a wash solution reservoir, the control unit being configured to actuate the valves to deliver the wash solution and the gas.

8. The apparatus of claim 7, wherein the control unit is configured to actuate the valves in response to a signal received at the control unit.

9. The apparatus of claim 1, further comprising markings disposed on the proximal portion of the main body, the markings configured to provide a visual cue to assist a user in positioning the endoscope for cleaning.

10. An apparatus, comprising:

a main body having a wall defining a lumen configured to receive an endoscope, the main body having a distal end configured to allow the endoscope to extend distally therethrough and into a body lumen;

an inlet port disposed on a proximal portion of the main body and configured to receive a wash solution and a gas;

a cleaning orifice disposed on the wall near the distal end and facing inward toward the lumen, the cleaning orifice configured to deliver the wash solution and the gas into the lumen as an atomized spray to clean a distal end of the endoscope; and a fluid channel disposed in the wall of the main body, the fluid channel configured to fluidically couple the inlet port to the cleaning orifice, the fluid channel having rounded edges without steps or corners such that the fluid channel is configured to reduce retention of fluid within the fluid channel while the wash solution and the gas are delivered to the cleaning orifice.

11. The apparatus of claim 10, wherein the fluid channel has a first rounded edge positioned proximate to the inlet port and a second rounded edge positioned proximate to the cleaning orifice.

12. The apparatus of claim 11, wherein the first rounded edge curves in a first direction and the second rounded edge curves in a second direction different from the first direction.

13. The apparatus of claim 10, wherein the rounded edges are configured to change a direction of a flow of the wash solution and the gas being delivered therethrough.

14. The apparatus of claim 10, wherein the fluid channel has an ovular cross-sectional shape.

15. The apparatus of claim 10, wherein the main body has a shaped end including a first edge and a second edge opposite the first edge, the first edge extending further distally than the second edge, the fluid channel and the cleaning orifice being disposed in the wall of the main body on a side including the first edge.

16. The apparatus of claim 10, further comprising markings disposed on the proximal portion of the main body, the markings configured to provide a visual cue to assist a user in positioning the endoscope for cleaning.

17. A method, comprising:

receiving a wash solution and a pressurized gas at an inlet port of an endoscope cleaning device, the endoscope cleaning device having a main body that defines a lumen configured to receive an endoscope, the inlet port being in fluid communication with a cleaning orifice disposed adjacent to a distal end of the main body;

in response to a distal end of the endoscope being retracted from a position disposed distally of the distal end of the main body to a position proximal of the distal end of the main body and inside of the lumen, delivering, via the cleaning orifice, the wash solution propelled by the pressurized gas as a spray directed toward the distal end of the endoscope to clean the distal end of the endoscope received within the lumen; and delivering, after delivering the wash solution, additional pressurized gas into the lumen to dry the distal end of the endoscope.

18. The method of claim 17, further comprising:

receiving a signal at a control unit operatively coupled to valves that are coupled to a gas supply and a wash solution reservoir; and actuating, with the control unit, the valves to deliver the wash solution and the pressurized gas into the inlet port.

19. The method of claim 18, wherein the control unit is further configured to generate visual or audible feedback to assist a user in positioning the endoscope for cleaning.

20. The method of claim 17, further comprising loading, after delivering the additional pressurized gas, an amount of the wash solution into a fluid channel coupled to the cleaning orifice to prime the endoscope cleaning device for a subsequent cleaning operation.

* * * * *